United States Patent
Boluk et al.

(10) Patent No.: US 9,744,270 B2
(45) Date of Patent: Aug. 29, 2017

(54) NANOCRYSTALLINE CELLULOSE HYDROGELS FOR INHIBITION OF BACTERIAL ADHESION

(71) Applicant: The Governors of the University of Alberta, Edmonton (CA)

(72) Inventors: Yaman Boluk, Edmonton (CA); Yang Liu, Edmonton (CA); Xiaohui Sun, Edmonton (CA)

(73) Assignee: The Governors of the University of Alberta, Edmonton, AB (CA)

( * ) Notice: Subject to any disclaimer, the term of this patent is extended or adjusted under 35 U.S.C. 154(b) by 0 days.

(21) Appl. No.: 14/898,944

(22) PCT Filed: Jun. 20, 2014

(86) PCT No.: PCT/IB2014/001542
§ 371 (c)(1),
(2) Date: Dec. 16, 2015

(87) PCT Pub. No.: WO2014/203075
PCT Pub. Date: Dec. 24, 2014

(65) Prior Publication Data
US 2016/0346436 A1    Dec. 1, 2016

Related U.S. Application Data

(60) Provisional application No. 61/837,329, filed on Jun. 20, 2013.

(51) Int. Cl.
A61L 29/08    (2006.01)
C08J 3/075    (2006.01)
A61L 29/04    (2006.01)
A61L 29/14    (2006.01)

(52) U.S. Cl.
CPC .......... *A61L 29/085* (2013.01); *A61L 29/041* (2013.01); *A61L 29/14* (2013.01); *A61L 29/145* (2013.01); *C08J 3/075* (2013.01); *A61L 2420/06* (2013.01); *C08J 2301/02* (2013.01)

(58) Field of Classification Search
None
See application file for complete search history.

(56) References Cited

U.S. PATENT DOCUMENTS

| 7,393,501 B2 | 7/2008 | Zumeris et al. |
| 7,829,029 B2 | 11/2010 | Zumeris et al. |
| 8,133,580 B2 | 3/2012 | Dias et al. |
| 8,641,686 B2 | 2/2014 | Stephan |
| 8,741,855 B2 | 6/2014 | Quave et al. |
| 2009/0255536 A1 | 10/2009 | Av-Gay et al. |
| 2011/0091551 A1 | 4/2011 | Baur et al. |
| 2011/0150961 A1* | 6/2011 | Perry ............... A61K 31/74 424/411 |
| 2012/0203211 A1* | 8/2012 | Weadock ......... A61M 25/0017 604/544 |
| 2013/0046275 A1 | 2/2013 | Holzer et al. |
| 2013/0195841 A1 | 8/2013 | Gabbay |
| 2014/0205586 A1 | 7/2014 | Xi et al. |

FOREIGN PATENT DOCUMENTS

| CA | 2335055 A1 | 12/1999 |
| CA | 2734778 A1 | 2/2010 |
| WO | 03099100 A2 | 12/2003 |
| WO | 2006063176 A2 | 6/2006 |
| WO | 2013192300 A1 | 12/2013 |

OTHER PUBLICATIONS

Klemm, D., et al., Macromol. Symp. 280: 60-71 (2009).*
Boluk, Yaman, et al., "Dispersions of Nanocrystalline Cellulose in Aqueous Polymer Solutions: Structure Formation of Colloidal Rods," Langmuir, 2012, 6114-6123, 28.
International Search Report dated Mar. 13, 2015, Application No. PCT/IB2014/001542, filed Jun. 20, 2014.
Sun, Xiaohui, et al., "Flocculation of bacteria by depletion interactions due to rod-shaped cellulose nanocrystals," Chemical Engineering Journal, 2012, 476-481, 198-199.
Written Opinion dated Mar. 13, 2015, Application No. PCT/IB2014/001542, filed Jun. 20, 2014.

* cited by examiner

*Primary Examiner* — David J Blanchard
*Assistant Examiner* — Daniel F Coughlin
(74) *Attorney, Agent, or Firm* — Haukaas Fortius PLLC; Michael H. Haukaas

(57) ABSTRACT

The invention provides compositions for the inhibition of bacterial adhesion. The composition can include nanocrystalline cellulose (NCC) and a water-soluble polymer, which form an NCC hydrogel in water. The NCC hydrogel can be used to treat or coat devices such as a catheter, whereby the NCC hydrogel inhibits bacterial adhesion to the catheter surface to thereby inhibit biofilm formation and growth of bacteria on the catheter surface. The compositions and devices can thus be useful for inhibiting or preventing conditions such as urinary tract infections.

18 Claims, 12 Drawing Sheets

A.

B.

A.

B.

A.

B.

A.

B.

C.

D.

A.

B.

NANOCRYSTALLINE CELLULOSE HYDROGELS FOR INHIBITION OF BACTERIAL ADHESION

RELATED APPLICATIONS

This application is a National Stage filing under 35 U.S.C. §371 of International Application No. PCT/IB2014/001542, filed Jun. 20, 2014, which claims priority under 35 U.S.C. §119(e) to U.S. Provisional Patent Application No. 61/837,329, filed Jun. 20, 2013, which applications are incorporated herein by reference.

BACKGROUND OF THE INVENTION

Urinary catheters are highly associated with urinary tract infections (UTIs) and the widespread use of urinary catheterization in hospitals and long-term care facilities is believed to be one of the most common causes of health care-associated infections. Urinary catheter-associated bacteriuria accounts up to 80% of urinary tract infections (UTI) and is a common infection related to medical devices in hospitals and long-term care facilities. Every year, more than 25% of patients treated with urinary catheters suffer from catheter-associated urinary tract infection (CA-UTI). The colonization of urinary catheters by uropathogenic organisms by formation of biofilms is a main cause of the onset of UTIs.

Biofilms are organized multicellular communities of bacteria attached to a surface and embedded in a protective polymer matrix. The biofilm phenotype is a ubiquitous characteristic of bacteria that constitutes a protected growth mode to facilitate survival of the bacteria in hostile environments. Biofilms provide increased resistance to host defenses and antimicrobials. Consequently, infections involving biofilms are notoriously difficult to treat and commonly manifest as chronic or recurrent infections. Current antibiotic agents often fail to halt biofilm formation and may potentiate the growth of antibiotic-resistant bacteria. Disruptive technologies are urgently needed to offer alternative treatments that inhibit biofilm formation processes such as compositions and methods to reduce or inhibit bacterial adhesion and the formation of biofilms.

SUMMARY

The invention provides a nanocrystalline cellulose (NCC) hydrogel-installed medical device, such as a catheter, that can inhibit or prevent urinary tract infections during catheterization. Nanocrystalline cellulose (NCC) is 99% effective for reducing initial bacterial adhesion (by depletion of colonization-induced bacterial flocculation) and subsequent biofilm formation on various material surfaces.

In addition, the invention provides a slow-release of NCC by the application of NCC-based hydrogels on various surfaces. The hydrogel can elute and coat an entire surface, such as a catheter or drainage bag surface, to prevent bacterial adhesion and biofilm formation and progress into the body from an indwelling catheter. Applying NCC hydrogels to catheters can be highly effective to reduce UTIs caused by bacterial adhesion and biofilm formation in catheters. Moreover, NCC does not have antibiotic effects and therefore reduces the preferential growth of antibiotic-resistant bacteria.

We discovered an effective anti-biofilm nanocrystalline cellulose (NCC) hydrogel-based system and have shown that it can prevent 99% of bacterial adhesion to common catheter material surfaces such as silicone, polyvinyl chloride, and latex rubber. The NCC-hydrogel can be readily installed onto catheters and a variety of other medical devices. NCC is biocompatible and non-toxic. The NCC-hydrogel system can be installed on currently commercially available catheters, for example, by simple brushing or spray-coating. The NCC-hydrogel system can reduce catheter-associated urinary tract infections (CA-UTI) by preventing biofilm formation, instead of by antimicrobial action. Installing the NCC-hydrogel system in urethral catheters can significantly reduce the high societal burden and medical costs associated with CA-UTI.

Accordingly, the invention provides a catheter comprising a nanocrystalline cellulose (NCC) hydrogel coating for inhibiting urinary tract infections, whereby the NCC hydrogel inhibits bacterial adhesion to the catheter surface to thereby inhibit biofilm formation and growth of bacteria on the catheter surface. The invention further provides a device for preventing CA-UTIs on a urinary catheter comprising a catheter coated with a nanocrystalline cellulose (NCC) hydrogel.

The catheter surface can be of any suitable and effective catheter material such as is found in various commercially available catheters. Examples of the surface material of the catheters can include silica, silicone, polyvinyl chloride, latex rubber, or a combination thereof. The catheters can optionally include antibiotic coatings.

The NCC hydrogel can include NCC, a water-soluble polymer, and water, and optionally one or more other components to modify the clarity or viscosity of the hydrogel. In some embodiments, the NCC hydrogel comprises about 1-20 wt. % NCC, 1-10 wt. % NCC, 10-20 wt. % NCC, or about 2-5 wt. % NCC, with respect to the mass of the water-soluble polymer. The NCC and water-soluble polymer can together be about 0.1 wt. % to about 10 wt. % of the mass of the NCC hydrogel.

The water-soluble polymer of the hydrogel can be a cellulosic polymer such as hydroxyalkyl cellulose or a carboxyalkyl cellulose, or a water-soluble polymer with similar gelling properties. Specific examples of suitable and effective polymers include 2-hydroxyethyl cellulose (HEC) and carboxymethyl cellulose (CMC).

The pH of the NCC hydrogel can be modified to increase the bacterial aggregation properties of the hydrogel. In some embodiments, the pH of the NCC hydrogel can be about 5 to about 7.5, about 5.4 to about 7.3, about 6 to about 7.2, about 6.4 to about 7.4, or about 6.5 to about 7.2. The pH can be adjusted by standard techniques, such as by the addition of an appropriate amount of sodium hydroxide. The ionic strength of the NCC hydrogel can also be adjusted, for example, to about 5 mM to about 50 mM, about 5 mM to about 40 mM, about 10 mM to about 30 mM, about 5 mM to about 25 mM, or to about 10 mM. The ionic strength of the NCC hydrogel can be adjusted by standard techniques, such as by the addition of an appropriate amount of sodium chloride.

The invention also provides methods of reducing bacterial adhesion to a surface, or for preventing bacterial adhesion to a surface. The method can include contacting bacteria on or in proximity to a surface with nanocrystalline cellulose (NCC) or a NCC hydrogel composition as described herein, thereby causing flocculation or aggregation, and thereby reducing the adhesion of the bacteria to the surface. The methods are particularly effective for bacteria that produce high amounts of extracellular polymeric substance (EPS).

The bacteria can be in a dispersion and form flocs or aggregates in the presence of the nanocrystalline cellulose (NCC).

In some embodiments, the nanocrystalline cellulose (NCC), or the NCC hydrogel composition, is present in a coating, film, textile, or reinforcing filler, for example, on a medical device such as a catheter. The surface can be a silica surface, a silicone surface, a polyvinyl chloride surface, a latex rubber surface, or a combination thereof.

The invention further provides methods of inducing bacterial aggregation comprising contacting bacteria with nanocrystalline cellulose (NCC), or with a NCC hydrogel composition as described herein, thereby causing aggregation, and thereby reducing the ability of the bacteria to adhere to a surface. The invention yet further provides a method of inhibiting biofilm formation comprising contacting a bacteria-containing biofilm with nanocrystalline cellulose (NCC), or with a NCC hydrogel composition as described herein, thereby causing aggregation, and thereby inhibiting the formation of a biofilm.

In another embodiment, the invention provides a device for preventing catheter associated urinary tract infections on a urinary catheter comprising a catheter coated with a nanocrystalline cellulose (NCC) hydrogel. The NCC hydrogel can include NCC, a water-soluble polymer, and water; wherein the NCC hydrogel comprises about 1-20 wt. % NCC with respect to the mass of the water-soluble polymer; the pH of the NCC hydrogel is about 6.2 to about 7.3; and the ionic strength of the NCC hydrogel is about 5 mM to about 40 mM.

Furthermore, the invention provides a hydrogel composition comprising nanocrystalline cellulose (NCC), a water-soluble polymer, water, and one or both of humic acid and a saccharide, wherein the hydrogel comprises about 1-20 wt. % NCC with respect to the mass of the water-soluble polymer, the NCC and water-soluble polymer comprise about 0.1 wt. % to about 10 wt. % of the mass of the NCC hydrogel, and the humic acid or saccharide is present in a concentration of about 0.1 mg/mL to about 10 mg/mL.

The compositions described herein can thus be used to reduce the frequency or severity of infections related to the use of medical devices, for example, infections such as catheter-associated urinary tract infections.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
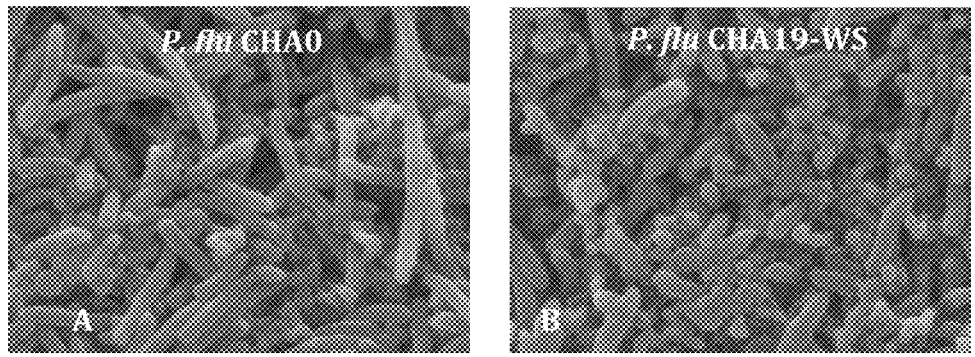
FIG. 1. Representative SEM micrographs of (A) P. flu CHA0 and (B) P. flu CHA19-WS.

Bacterial aggregation and adhesion commonly results in the formation of bioflocs and biofilms in many industrial, environmental and medical environments. Inhibition or prevention of bacterial aggregation and adhesion is thus critical for effective and safe use of devices in these arenas. Aggregation and adhesion of bacteria, like other inert colloids, depends on Van der Waals and electrostatic interactions, hydrophobic, and steric forces between bacterial cells and surfaces. However, the complex and heterogeneous surface structures of bacteria, such as their surface appendages, complicate the interaction between bacteria and other bacteria, and between bacteria and substratum surfaces. Thus, bacterial aggregation and adhesion are also associated with the physicochemical properties of the bacterial surface. Bacterial surface appendages, such as extracellular polymeric substances (EPS), contribute to bacterial aggregation and adhesion, although their presence cannot be expressed with microbial contact angles and zeta potential measurements.

Bacterial adhesion to a solid surface consists two major steps. First, the bacterial cells transport to a solid surface, which transport is controlled by the size of the cells and hydrodynamics of the system. Second, is the subsequent interaction between a cell and the surface occurring upon close approach, which is determined by DLVO (Derjaguin-Landau-Verwey-Overbeek theory)-type steric, hydrophobic, and hydration interactions. Moreover, in the flow regime (simple share systems), fluid drag effects (hydrodynamic forces) on bacterial deposition can be taken into account.

Extracellular polymeric substances (EPS) are comprised of polysaccharides, proteins, nucleic acids, humic-like substances, lipids, and heteropolymers. The excretion of EPS is one of the basic biological characteristics of bacteria. It is well documented that EPS play an important role in bacterial aggregation and adhesion. A bacterial suspension can be considered a dispersion of colloids surrounded by non-adsorbing polyelectrolytes, and EPS, which can provide an attractive force to induce microbial aggregation in flocs and biological sludge, and to attach biofilms to solid surfaces. EPS is involved in the depletion attraction mechanism, which induces bacterial aggregation and phase separation of *Escherichia coli* cells.

Nanocrystalline cellulose (NCC) is a biodegradable and environmental friendly form of highly crystalline rod-like nanoparticles. The material has also been referred to as cellulose nanocrystals (CNC) or cellulose whiskers. Due to the high aspect ratio (length-to-width ratio) of NCC, NCC increases the strength and stiffness of materials to which it is added, and it can be used in coatings, films, textiles and reinforcing fillers. NCC can be prepared by hydrolysis of pure cellulose using sulfuric acid. Hydrolysis of cellulose by concentrated sulfuric acid in a controlled mode removes the amorphous regions (low crystallinity) of cellulose molecules and isolates the homogeneous regions (high crystallinity) representing the nanocrystals. NCC particles in aqueous solutions are negatively charged due to an esterification reaction introducing sulfate ester groups on their surface. Sulfuric acid processing of NCC surfaces can thus provide a stable suspensions in water (Boluk et al., *Langmuir* 2012, 28, (14), 6114-6123).

Our research has shown that rod-shaped NCC particles, even at low concentrations (relative to the model prediction), are very effective in agglomerating gram-negative EPS producing bacteria such as *Pseudomonas aeruginosa* PAO1 (Sun et al., *Chem. Eng. J.* 2012, 198, 476-481). The presence of EPS on *P. aeruginosa* PAO1 cell surfaces can contribute to low NCC concentrations needed to cause bacterial depletion aggregation. The extent of NCC-induced bacterial aggregation may vary depending on the capacity of bacterial cells to produce EPS, and that bacterial aggregation in the presence of NCC can subsequently impact their adhesion behaviors. The experiments described herein evaluate the impact of NCC particles on the aggregation and adhesion of bacterial cells with different EPS producing capabilities. The aggregation of bacteria was assessed by microscopy. The deposition of bacteria on solid surfaces was determined using heterotrophic plate counting and quartz crystal microbalance with dissipation (QCM-D).

Bacterial adhesion and biofilm development on solid surfaces is a survival strategy employed by virtually all bacteria. However, in the majority cases, bacterial colonization can be detrimental to both human life and industrial processes, causing pathogen contamination, corrosion, and biofouling. A preliminary step of biofilm formation is bacterial deposition and adhesion, which represent important control steps to prevent biofilm formation. The results described herein indicate that NCC can induce bacterial aggregation effectively, and thus inhibit subsequent bacterial adhesion. Under both static and hydrodynamic flow conditions applied, NCC's effect on bacterial aggregation caused a significant reduction in bacterial adhesion to silica surfaces. Thus, NCC can be used for creation and manipulation of bacterial flocs and for preventing bacterial adhesion and subsequent biofilm development. Artificial formation of bioflocs and altering the development of biofilms are useful processes in many applications involving biodegradation or bioremediation. Properties of the NCC and bacterial composition, such as pH and ionic strength, can also be used to increase the effect of the NCC on bacterial adhesion. Typically, increasing the pH of a composition or the environment of a bacterial suspension or biofilm (e.g., up to about 7.4 or 7.5) can increase the effectiveness of NCC on bacterial adhesion.

This disclosure shows that the addition of nanocrystalline cellulose (NCC) to bacteria reduces the adhesion of bacteria to surfaces. The NCC is particularly effective for reducing the adhesion of bacteria to surfaces that comprise a silica-based surface. The NCC is also highly effective at reducing the adhesion of bacteria that produce excess amounts of extracellular polymeric substance (EPS). Excess amounts of EPS can be determined visually by observation of SEM images. NCC and NCC hydrogels can be significantly more effective, for example, when at least 20-30% additional EPS is produced by bacteria in a particular environment.

Definitions

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. For example, the hydrogels described herein can include or exclude an antibiotic, for example, any of the antibiotic or antimicrobial compounds recited herein.

The term "and/or" means any one of the items, any combination of the items, or all of the items with which this term is associated. The phrase "one or more" is readily understood by one of skill in the art, particularly when read in context of its usage. For example, one or more can refer to one, one or two, one to three, one to four, one to ten, or one to one hundred, etc., depending on the context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a condition, or to bring about a recited effect. For example, an effective amount can be an amount effective to reduce the progression or severity of a condition or event being treated, such as the formation of a biofilm on a surface. Determination of an effective amount is within the capacity of persons skilled in the art in light of the disclosure provided herein. The term "effective amount" is intended to include an amount of a composition described herein, or an amount of a combination of compounds or compositions described herein, e.g., that is effective to treat or prevent a recited condition or event. Thus, an "effective amount" generally means an amount that provides the desired effect.

The terms "treating", "treat" and "treatment" can include (i) preventing a condition or event from occurring (e.g., prophylaxis); (ii) inhibiting a condition or arresting its development; (iii) relieving the condition; and/or (iv) diminishing symptoms or effects associated with the condition or event. Thus, the terms "treat", "treatment", and "treating" can extend to prophylaxis and can include prevent, prevention, preventing, lowering, stopping or reversing the progression or severity of the condition or situation being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, adhesion, biofilm, or group of cells. The inhibition can be greater than about 20%, 40%, 50%, 60%, 70%, 80%, 90%, 95%, or 99%, for example, compared to the growth or progression that occurs in the absence of the treatment or contacting.

The term "biofilm" refers to films formed by microbes, microorganisms, viruses, fungi, deposits, particles, pathogenic organisms, cells, and other bioactive materials. The term "pathogenic microorganisms" encompasses organisms, including bacteria or protozoans, that cause a disease and are harmful and infectious. The NCC hydrogels described herein are particularly effective for inhibiting biofilms that are produce by bacteria that produce high amounts of extracellular polymeric substance (EPS), such as *Pseudomonas fluorescence*, *Pseudomonas aeruginosa, Salmonella* spp., and *Klebsiella pneumoniae*.

The terms "nanocrystalline cellulose" (NCC) and "cellulose nanocrystals" (CNCs) are used interchangeably herein. Cellulose nanocrystals (CNCs) are rod-like nanoparticles typically 50 nm to 500 nm (or 150 nm to 300 nm) in length and 3-5 nm in width and 3-20 nm in height (having a square or rectangular cross-section) (often 4-10 nm in average diameter). They are about 50-90% crystalline (e.g., about 60-90% crystalline or about 54-88% crystalline). They can be obtained by extraction from plants and trees followed by chemical processing. CNCs have facile water-dispersibility without the use of surfactant.

Humic acid is known organic compound complex, and is a principal component of the major organic constituents of soil (humus) and peat. It is produced by biodegradation of dead organic matter. It is typically a complex mixture of several organic acids containing carboxyl and phenolate groups so that the mixture behaves functionally as a dibasic or tribasic acid. Humic acids can form complexes with ions to create humic colloids. Humic acids, such as IHSS Suwannee River Humic Acid Standard II 2S101H, are commercially available. Humic acid can be used to increase the aggregation-promoting properties of NCC. An effective amount of humic acid in combination with NCC, or in an NCC hydrogen, can be about 0.1 mg/mL to about 10 mg/mL, 0.5 mg/mL to about 5 mg/mL, or about 1 mg/mL.

The term "saccharide" refers to a sugar, such as a monosaccharide or a disaccharide. Typical monosaccharides include allose, altrose, glucose, mannose, gulose, idose, galactose, or talose. Typical disaccharides include sucrose, lactose, maltose, trehalose, and cellobiose. Disaccharides can have any suitable linkage between the first and the second unit of the disaccharide. Other suitable saccharides include glucuronic acid, sorbase, ribose, and the like. Saccharides, including monosaccharides and disaccharides, can be used to increase the aggregation-promoting properties of NCC. An effective amount of a saccharide in combination with NCC, or in an NCC hydrogen, can be about 0.1 mg/mL to about 10 mg/mL, 0.5 mg/mL to about 5 mg/mL, or about 1 mg/mL.

NCC-Hydrogel Catheters

The surface of the nanocrystalline cellulose (NCC) hydrogel-installed catheters can be made from a variety of standard catheter materials. Materials from which catheters can be made include silicone rubber, fluorocarbons (e.g., Teflon® materials), polyethylene (PE), polypropylene (PP), polyvinyl chloride (PVC), polyurethane (PU), polytetrafluoroethylene (PTFE), polyamides (e.g., Nylon® polyamide), polyethylene terephthalate (PET), glass, metal, and various nanofiber substrates. Coating these materials with a nanocrystalline cellulose (NCC) hydrogel can prevent or inhibit urinary tract infections during catheterization or other medical procedures.

The NCC hydrogel coating can be used in conjunction with other coatings such as the coating described by U.S. Pat. No. 8,133,580 (Dias et al.). While the NCC hydrogel is particularly useful for coating catheters, other articles may also benefit from NCC hydrogel coatings. Such articles include endoscopes and laryngoscopes, tubes for feeding or drainage or endotracheal use, guide wires, various barriers (e.g. gloves, condoms, wound dressings, contact lenses, implants, extracorporeal blood conduits), membranes (e.g. for dialysis, blood filters, devices for circulatory assistance), or surgical equipment. The coating can also be applied to non-medical articles such as packaging for foodstuff, razor blades, fishing nets, conduits for wiring, water pipes having a coating inside, water slides, sports articles, cosmetic additives, and mold release agents.

The data described herein shows that NCC can reduce bacterial adhesion, which is the initial step in biofilm formation. Thus, by reducing bacterial adhesion, biofilm formation can be inhibited and prevented, which is particularly important for many medical applications. The composition can be applied to medical devices such as catheters by a variety of methods including spraying, immersing, brushing, wiping on with a cloth, and the like.

A gel useful for reducing bacterial adhesion can be prepared by combining NCC with soluble polymers such as 2-hydroxyethyl cellulose (HEC) or carboxymethyl cellulose (CMC), or other carboxyalkyl or hydroxyalkyl celluloses and suitably similarly effective polymers. Suitable concentrations of the NCC can be about 1 wt. % to about 20 wt. %, for example, about 4-15 wt. %, about 4-8 wt. %, or about 8-15 wt. %, with respect to the polymer. The NCC-polymer mixture can then be dissolved in water to provide an NCC gel. The gel can include about 0.1 wt. % to about 10 wt. % of the NCC-polymer mixture in water (e.g., 0.1 wt. %, 0.2 wt. %, 0.25 wt. %, 0.5 wt. %, 0.75 wt. %, 1 wt. %, 2 wt. %, 3 wt. %, 4 wt. %, 5 wt. %, 7.5 wt. %, or 10 wt. %), and the gel can be used for coating various surfaces or devices to prevent or inhibit bacterial adhesion and biofilm formation.

Biofilms provide increased resistance to host defenses and antimicrobials. Because a catheter coated with a CNC hydrogel inhibits the formation of biofilms, the development of bacterial resistance to antibacterial compounds is reduced or eliminated. Accordingly, various antibiotics, such as chlorhexidine/silver sulfadiazine, minocycline/rifampin, and platinum/silver, can be included in or in combination with a hydrogel composition as described herein. Specific examples products and coatings that can be used in conjunction with the hydrogels described herein include Bard's VitaCuff, a silver-impregnated cuff that is included on its central line catheters. This cuff rests against the skin at the point of entry for the catheter. Teleflex/Arrow International's ARROWg+ard may also be used. This product is a chlorhexidine and silver sulfadiazine coating available for use on multiple catheter types. Harland Medical Systems produce a chlorhexidine and protamine sulfate coating that can be used in combination with a CNC hydrogel. Furthermore, Surface Solutions Group's FluoroMed AM product is a silver ion based coating for catheters, which can also be used in combination with a CNC hydrogel. Finally, minocycline/rifampine and chlorhexidine coatings can be used in combination with a CNC hydrogel. Antibiotic resistance is leading to concerns with the use of the antibiotic minocycline/rifampine coating and adverse reactions to chlorhexidine coatings are creating similar concerns to the chlorhexidine coatings. Thus, combining these products and antibiotics with a CNC hydrogel can alleviate these clinical complications.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

Examples

Example 1. Impact of Nanocrystalline Cellulose on the Adhesion of *Pseudomonas fluorescence* Bacteria Deposition of two *Pseudomonas fluorescence* strains (CHA0 and CHA19-WS) to silica surfaces was studied in both static and dynamic flow systems and in the absence and presence of nanocrystalline cellulose (NCC). The two strains possess different extracellular polymeric substance (EPS) producing capacity. Within the presence of NCC, bacteria with more EPS coverage aggregate more significantly compared to bacteria with less EPS coverage. NCC significantly reduced bacterial initial adhesion to silica surfaces. Bacteria deposition was hindered to a greater extent for bacteria with more EPS coverage than those with less EPS coverage. Quartz crystal microbalance with dissipation (QCM-D) was used to further analyze the mechanisms by which NCC reduced bacterial adhesion. The classic DLVO theory for colloid stability failed to predict the bacterial adhesion behavior in this study. Surface charge heterogeneity and surface roughness of both bacteria and silica surfaces provide an explanation for the deviation from DLVO curves of the observed adhesion.

1. Material and Methods.

1.1. Culturing and Characterization of Bacteria.

Green fluorescent protein (GFP) labeled, gram-negative strains of Pseudomonas fluorescence, wild type (P. flu CHA0, normal EPS production) and the mutant ΔgacS that can overproduce cellulose of the EPS (P. flu CHA19-WS, increased EPS production; WS (wrinkly spreader) indicates one colony morphology variant from biofilms of the AgacS strain) were selected to perform the bacterial aggregation and adhesion experiments. For each experiment, the two stored strains were each streaked onto a Luria-Bertani (LB) agar plate and then incubated at 30° C. overnight. A single colony from each plate was then transferred into 50 mL of LB broth and grown in a shaker incubator at 150 rpm and 30° C. for 18 hours. Thereafter, stationary-phase bacterial cells were harvested by centrifugation at 3000 g and 4° C. for 10 minutes. The pellets were resuspended in a 10 mM NaCl solution, prepared with reagent grade salt (Fisher Scientific Inc., U.S.) and Milli-Q water (18.2 MΩ, Millipore, Mississauga, ON, Canada) with no pH adjustment (pH 5.6-6.0), and sterilized by autoclave before use. All characterizations and experiments were conducted using these cell suspensions in 10 mM NaCl.

The centrifugation and re-suspension procedures were repeated three times to remove from the solutions traces of growth media and suspended EPS. A final cell density of $1.0 \times 10^8$ cells/mL was obtained by measuring the optical density (OD) at 600 nm with a UV spectrophotometer (Varian Inc., U.S.). Scanning electron microscopy (SEM) was employed to characterize the size and morphology of bacterial cells. The zeta potential and average hydrodynamic sizes of each strain were determined by dynamic light scattering (DLS) (Malvern Zetasizer Nano-ZS; Model: ZEN3600, Malvern Instruments Ltd, Worcestershire, UK) at 25° C. The zeta potential and particle size measurements were repeated in five independent experiments.

1.2. NCC Suspension Preparation and Characterization.

A stock suspension of 1.0% (wt) NCC was prepared by suspending NCC particles in 10 mM NaCl and sonicating the solution for 5 minutes in a ultrasonic bath to disperse the NCC particles. The NCC suspension was then filtered through a 0.45 μm membrane (Acrodisc® Syringe Filters with GHP Membrane, Pall Corporation, US) and stored at 4° C. prior to use in the bacterial aggregation and adhesion experiments. The size and zeta potential of the NCC particles were assessed by DLS measurements in 10 mM NaCl at 25° C. The size was then qualitatively compared with images from transmission electron microscopy (TEM).

1.3. Bacterial Aggregation Experiment.

In the aggregation experiment, 1 mL 1.0% (wt.) NCC suspension was added to 1 mL of the bacterial suspensions to achieve a volume fraction of $5 \times 10^{-3}$ mL NCC/mL bacteria. Treatment controls without added NCC were also prepared. The whole system was incubated statically at 24° C. for 30 minutes before bacterial cells were dropped on clean microscopy glass slides (the cleaning protocol is provided in the Experimental Details section below) to facilitate fluorescent microscopic observations. Microscopic visualization of the slides was carried out under fluorescent light using an Axio Imager M2 microscope (Carl Zeiss, Germany) with a Zeiss LD Plan-NEOFLUAR 40× objective. At least ten images of randomly chosen areas of each slide were taken, and the number and size (radius) of bacterial aggregates in each image were obtained through counting ten areas of the image before averaging the results. These experiments were conducted in triplicate in at least five independent experiments.

1.4. Bacterial Initial Adhesion Experiment Under Static Conditions.

Bacterial initial adhesion on solid surfaces was investigated in 10 mM NaCl using a static soaking method by immersing microscopy glass slides in each bacterial suspension. For each adhesion experiment, fresh P. flu CHA0 and P. flu CHA19-WS bacterial suspensions ($1.0 \times 10^8$ cells/mL in 10 mM NaCl) were prepared as described in section 1.1 above. One mL was distributed in each well of a 24-well plate (Corning Inc., U.S.) and then 1 mL of 1.0% (wt) NCC suspension was added to each well. The cleaned glass slides were completely submerged in the bacterial suspension for 30 minutes at 24° C. in a static state. Then the bacterial suspension was removed and the glass slides were rinsed with 10 mM NaCl solution to remove loosely attached cells.

To observe the differences before and after NCC treatment for each strain, bacterial enumeration was performed by heterotrophic plate counting (HPC) using the drop plate method (Liu et al., J. Photochem. Photobiol. a-Chem. 2007, 190, (1), 94-100). Briefly, after each adhesion experiment, the bacteria-coated slides (after removal of loosely attached cells) were placed in glass tubes with 1 mL Milli-Q water followed by 10 minutes of ultrasonication. Pilot *fluorescence* microscopy showed that this ultrasonication process was effective to detach the attached bacterial cells from the glass slides. A series of 10-fold dilutions using Milli-Q water was performed and 10 μL of each dilution was plated on an LB agar plate in triplicate. Plates were incubated at 30° C. for 24 hours. Counting was performed after 24 hours to determine bacterial viability. The lower detection limit is $10^2$ CFU/mL. Bacterial adhesion experiments were conducted in triplicate in at least five independent experiments. The variance of bacterial adhesion was analyzed with a one-way analysis of variance (ANOVA) and was reported as p-values. P-values of less than 0.05 indicate differences are statistically significant.

1.5. Quartz Crystal Microbalance with Dissipation (QCM-D) Bacterial Adhesion Study.

QCM-D is an advanced technology for the study of surface interactions and provides real-time, label-free measurements of molecular adsorption and/or interactions taking place on surfaces. Based on the piezoelectric effect, the frequency change (Δf) of a quartz crystal sensor corresponds to the mass loaded on the quartz surface; the dissipation (ΔD) change indicating the energy dissipation response of the freely oscillating sensor corresponds to the viscoelastic properties of molecular layers as they build up or change on the quartz surface. The QCM-D technique is sensitive to measure nanograms of mass and can be applied to in situ structural arrangements, thus it is a useful technique to provide further insight into the mechanisms and strength of cell adhesion to surfaces.

To further analyze the mechanisms of impact of NCC on bacterial initial adhesion, deposition of bacteria to silica coated quartz surfaces (with a fundamental resonant frequency of approximately 5 MHz, QSX-303, Q-sense AB, Gothenburg, Sweden) was studied using QCM-D (Q-sense E4, Biolin Scientific, Sweden). All QCM-D experiments were performed under flow-through conditions, using a digital peristaltic pump (ISMATEC, IPC high precision multichannel dispenser) operating in pushing mode, with the studied solutions injected to the sensor crystal chamber at 0.15 mL/min. Prior to each experiment, the cleaned silica surface was equilibrated by pumping of a bacteria- and NCC-free background 10 mM NaCl solution. The 1.0% NCC suspension, bacterial suspension, and bacterial suspension supplemented with NCC (5 mL bacteria suspension in 10 mM NaCl with 5 mL 1.0% NCC) were then each injected for 30 minutes to assess the bacterial deposition behaviors. Following the injection, silica surfaces were eluted with background 10 mM NaCl to assess bacterial adhesion stability. The sample solutions in the chamber were maintained at 24° C. In contrast to the static systems, QCM-D experiments allow continuous, noninvasive monitoring of bacterial adhesion, which reflects the natural environment where the organisms reside.

1.6. DLVO Interaction Energy Calculations.

The initial adhesion of bacteria to solid substratum in aquatic systems is generally considered to be similar to the deposition of colloidal particles. Thus, classic DLVO theory has been widely applied to explain bacterial adhesion behaviors. Classic DLVO theory describes total energies $\Delta G^{TOT}$ between bacteria and substratum in solution as a balance between attractive Lifshitz-van der Waals $\Delta G^{LW}$ and electrostatic $\Delta G^{EL}$ interaction energies as a function of separation distance d (Eq. 1).

$$\Delta G^{TOT}(d)_{classical} = \Delta G^{LW}(d) + \Delta G^{EL}(d) \quad (1)$$

Bacterial adhesion to a substratum surface can be assumed as a sphere (radius of a) approaching a semi-infinite plate. $\Delta G^{LW}(d)$ and $\Delta G^{EL}(d)$ are expressed in Equation 2:

$$\Delta G^{LW}(d) = -\frac{Aa}{6d} \quad (2)$$

$$\Delta G^{EL}(d) = \pi \varepsilon a (\zeta_1^2 + \zeta_2^2) \left[ \frac{2\zeta_1 \zeta_2}{\zeta_1^2 + \zeta_2^2} \ln \frac{1+\exp(-\kappa d)}{1-\exp(-\kappa d)} + \ln\{1 - \exp(-2\kappa d)\} \right]$$

A, $\varepsilon$, $\zeta$, and $\kappa^{-1}$ are the Hamaker constant, the permittivity of the medium, the zeta potential, the Debye length, respectively. The input parameters needed to describe the electrostatic and van der Waals forces for sphere-plate interactions are shown in Table 1 below.

TABLE 1

Input parameters in the DLVO calculations.

| Symbol | Value used |
|---|---|
| $a_1$, equivalent radius of P. flu CHA0 cells (m) | $4.4 \times 10^{-7}$ |
| $a_2$, equivalent radius of P. flu CHA19-WS cells (m) | $4.1 \times 10^{-7}$ |
| $a_3$, equivalent radius of CNC particles (m) | $4.6 \times 10^{-9}$ |
| $\zeta_1$, zeta potential of P. flu CHA0 (mV) | −18.78 |
| $\zeta_2$, zeta potential of P. flu CHA19-WS (mV) | −16.22 |
| $\zeta_3$, zeta potential of CNC (mV) | −42.30 |
| $\zeta_4$, zeta potential of glass surface/silica crystal surface (mV) | −36.30 |
| A, Hamaker constant (J) | $6.16 \times 10^{-21}$ [a, b] |
| relative permittivity | 80.1 |

TABLE 1-continued

Input parameters in the DLVO calculations.

| Symbol | Value used |
|---|---|
| vacuum permittivity | $8.854 \times 10^{-12}$ |
| $\kappa^{-1}$, Debye length (m) | $3.3 \times 10^{8}$ |

[a] Rijnaarts et al., Colloids and Surfaces B: Biointerfaces 1995, 4, 5-22.
[b] Rijnaarts et al., Colloids and Surfaces B: Biointerfaces 1995, 4, 191-197.

2. Results and Discussion.

2.1. Characterization of Bacterial Cells and NCC Particles.

The wild type strain P. flu CHA0 is reported to have normal EPS production, while the mutant strain P. flu CHA19-WS has increased EPS production. As shown in FIG. 1, both strains were rod-shaped and equipped with thread-like EPS appendages. More EPS coverage was observed on P. flu CHA19-WS (FIG. 1B) than on P. flu CHA0 (FIG. 1A). The results are consistent with the fact that P. flu CHA19-WS can overproduce cellulose of the EPS. DLS measurements showed that the diameter of the P. flu CHA0 cells (1.76±0.07 µm; corresponding to an equivalent radius of 0.44 µm) was longer than that of the P. flu CHA19-WS cells (1.44±0.03 µm; corresponding to an equivalent radius of 0.41 µm), which was confirmed by SEM image analysis (FIG. 1). In addition, under the experimental conditions, the two strains displayed significantly different (p=$1.9 \times 10^{-4}$) negative zeta potential values, −18.78±1.31 my and −16.22±0.89 my for P. flu CHA0 and P. flu CHA19-WS, respectively.

Figure 2:
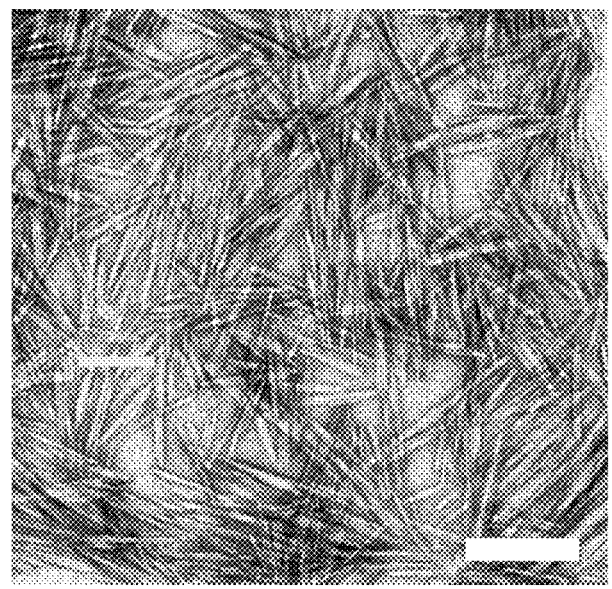
FIG. 2. TEM image of NCC particles (bar size=200 nm).

FIG. 2 shows a TEM image of rod-shaped NCC particles with a length of 100-200 nm and a width (radius) of around 10 nm; the size of the NCC particles measured using DLS was 114±2.13 nm. The zeta potential of the NCC particles in 10 mM NaCl solution was −42.3±1.07 my, indicating negatively charged surfaces which can be attributed to the sulfate ester groups introduced by the esterification reaction during hydrolysis.

2.2. Role of EPS in NCC-Induced Bacterial Aggregation.

Fluorescent microscopy images of bacterial aggregation were obtained for P. flu CHA0 without and with NCC; and for P. flu CHA19-WS without and with NCC. Without NCC, the two strains were well dispersed, free of flocculate (average radius=0.44 µm and 0.41 µm for P. flu CHA0 and P. flu CHA19-WS, respectively, calculated based on the DLS measurements), and the culture chamber liquid was observed to be turbid. With the addition of NCC, P. flu CHA19-WS showed very significant aggregation and formed large, dense bacterial aggregates (average radius=4.5 µm), while P. flu CHA0 formed small, loose bacterial aggregates (average radius=2 µm). These results indicate that without NCC application, flocs were unlikely to form. With the addition of NCC, average radii of aggregates can be increased by 5 times to about 10 times.

Based on depletion mechanism, the addition of repelling NCC particles into the dispersion of bigger colloidal bacterial cells destabilizes the system. Rod-shaped NCC particles are very efficient at depletion aggregation of gram-negative bacteria such as *Pseudomonas aeruginosa* PAO1. Theoretical calculations of the depletion potential (detailed calculations and formulas are provided in the Experimental Details section below) under the test conditions indicate depletion aggregation was unlikely to occur, due to the low NCC concentration added in the system; volume concentration of $1 \times 10^{-2}$ mL NCC/mL bacteria is needed based on the model predication and $5 \times 10^{-3}$ mL NCC/mL bacteria was used in the present study. Similar results were observed in our studies on the depletion aggregation of *P. aeruginosa* PAO1 using NCC. The deviation of the observed aggregation from predicted depletion potentials may be explained in the following three ways.

First, the formula (Equation (3) in the Experimental Details section) used in the depletion potential calculations is ideally for large spherical particles in the presence of small, rod-shaped particles, while the bacterial cells studied in the current study are cylindrically shaped.

Second, the deviation in potentials can be the result of the EPS, which may impose polymer-mediated steric interactions, such as polymer bridging, and contribute to depletion aggregation; these interactions were not considered in the predicted depletion potentials. This can be explained by the fact that EPS surrounding the bacterial cells can trigger a depletion attraction between bacterial cells. Because of the presence of both EPS and NCC in the suspension, the interaction between NCC and bacterial cells determines the mechanism of the destabilization; repulsive interactions between like-charged bacterial cells lead to depletion, whereas the presence of EPS may impose polymer bridging, resulting in more significant aggregation of the more EPS-covered strain *P. flu* CHA19-WS.

Third, the surface charge of bacterial cells may also play an important role in bacterial aggregation. The less negatively charged *P. flu* CHA19-WS decreased the electrostatic repulsive forces between cells resulting in more significant aggregation. The composition and charge of EPS vary depending on bacterial strains, which makes the interaction between bacteria and NCC particles more complicated compared to ideal colloids and deserves further study. Compared to our previous study, where NCC induced much more significant aggregation of *P. aeruginosa* PAO1, the current study showed less significant aggregation of the two *P. fluorescence* strains, likely explained by the fact that *P. aeruginosa* PAO1 used in the previous study is more negatively charged (−29.84 mV) than are *P. fluorescence* strains (−18.78 and −16.22 mV respectively) as used in the current study.

2.3. Impact of EPS on NCC-Induced Reduction in Initial Bacterial Adhesion.

2.3.1 Bacterial Initial Adhesion Under Static Conditions.

Figure 3:
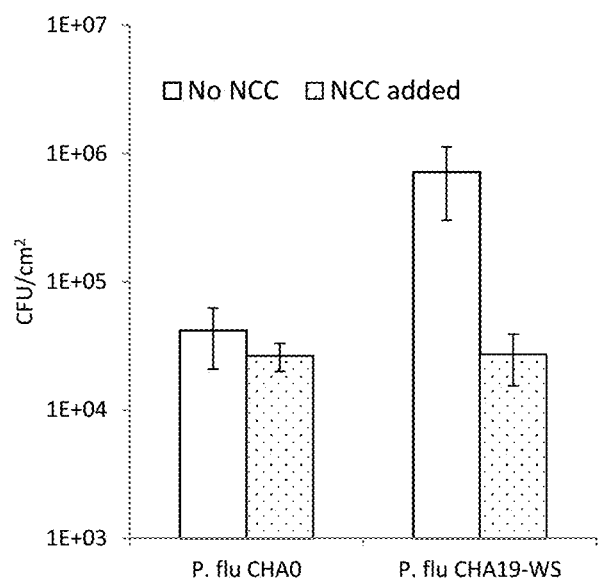
FIG. 3. Enumeration of bacterial static adhesion. Each data point represents the average of three measurements for one sample. Error bars represent the standard deviation.

FIG. 3 illustrates the enumeration of the cell density of each strain deposited on glass slides, determined from colony forming unit counts. As can be seen in the figure, in the absence of NCC, *P. flu* CHA19-WS showed a slightly higher (p=0.049) adhesion capability ($7.14 \times 10^5$ CFU/cm$^2$) than did *P. flu* CHA0 ($4.17 \times 10^4$ CFU/cm$^2$). The variation can be explained by the fact that *P. flu* CHA19-WS is less negatively charged than the wild type *P. flu* CHA0. It should also be noted that the higher EPS coverage and the smaller cell dimension of the *P. flu* CHA19-WS strain, in comparison to its wide type strain, may play an important role in controlling their initial adhesion on glass surfaces. In a bacterial adhesion kinetic study using a radial stagnation point flow system, Chen et al. (*Langmuir* 2007, 23, (13), 7162-7169) indicated greater bacterial adhesion to quartz surface was resulted from more EPS covered and smaller sized bacteria.

After the addition of NCC, deposition of *P. flu* CHA19-WS onto glass slides was significantly (p=0.045) inhibited and achieved about 1.7 log-unit reduction (~98%) in cell density, while NCC did not significantly (p=0.24) reduce the deposition of *P. flu* CHA0 onto glass slides.

2.3.2 Bacterial Initial Adhesion Under Dynamic Flow Conditions.

Bacterial initial adhesion under dynamic flow conditions (flow rate=0.15 mL/min) was studied using a QCM-D coupled with a *fluorescence* microscope. Frequency shifts ($\Delta F$) and dissipation change ($\Delta D$) with time were monitored in the QCM-D bacterial adhesion experiments, where generally a large $\Delta F$ indicates a large mass load on silica surfaces and a large $\Delta D$ indicates a soft mass load on silica surfaces.

Figure 4A:
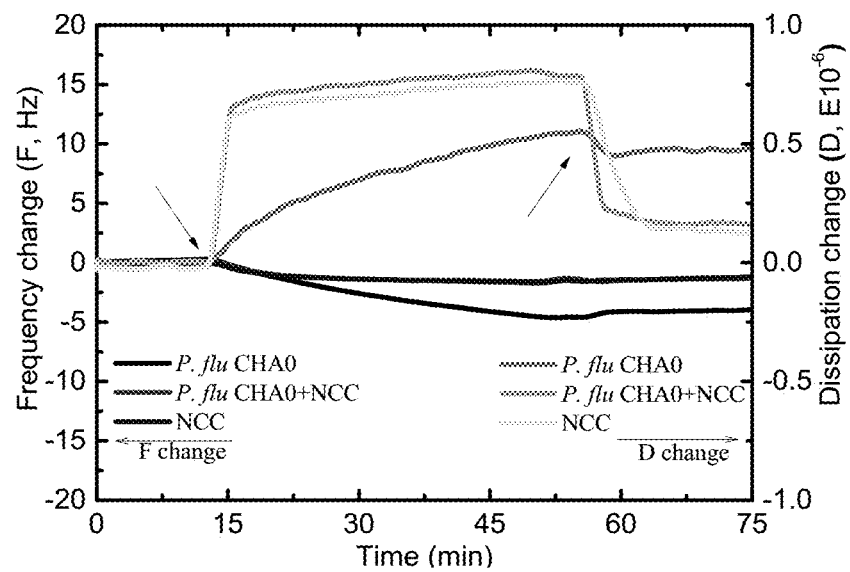
FIG. 4. QCM-D adhesion results. The frequency change ΔF and dissipation change ΔD responses for the adsorption of NCC, bacteria with NCC and bacteria respectively obtained from QCM-D measurements. Solutions were sequentially pumped through the $SiO_2$ sensor surface in the following order: 10 mM NaCl (0-10 min, flat line in the figure), samples (NCC, mixture of bacteria and NCC, bacteria) in 10 mM NaCl (starting from the arrowed position), and 10 mM NaCl (starting from the arrowed position) at 0.15 mL/min. (A) Adsorption profile of P. flu CHA0 with and without NCC; (for frequency change: P. flu CHA0, lowest line; P. flu CHA0+NCC, overlapping middle line near 0; NCC, overlapping middle line near 0; for dissipation change: P. flu CHA0, line ending near 0.5; P. flu CHA0+NCC, highest line; NCC, second highest line); (B) Adsorption profile of P. flu CHA19-WS with and without NCC; (for frequency change: P. flu CHA19, lowest line; P. flu CHA19+NCC, middle line nearest 0; NCC, near-middle line ending near −0.5; for dissipation change: P. flu CHA19, line ending between 0.25 and 0.5; P. flu CHA19+NCC, second highest line; NCC, highest line); (C) cell density (cells/cm$^2$) on silica surface after QCM-D adhesion experiments. Each data point represents the average of three measurements for one sample. Error bars represent the standard deviation.

As shown in FIG. 4A, adsorption occurred as soon as the sample solution made contact with the silica surface. The adsorption of NCC without bacteria reached a plateau of around 1.75 Hz after about 50 min NCC injection. The $\Delta F$ of *P. flu* CHA0 without NCC achieved a frequency shift ($\Delta F$) up to around 4.5 Hz after 55 min, while $\Delta F$ of the *P. flu* CHA0 supplemented with NCC was significantly lowered (1.75 Hz), and was the same as that of NCC. The lower frequency change of the *P. flu* CHA0 supplemented with NCC than that of solely *P. flu* CHA0 indicates that *P. flu* CHA0 adhesion onto silica surface was inhibited by NCC. Adsorbed NCC and *P. flu* CHA0 supplemented with NCC were desorbed slightly upon rinsing with background solution (10 mM NaCl), while adsorbed *P. flu* CHA0 desorbed significantly and reached a final $\Delta F$ of around 4 Hz. The desorption indicates that these bacteria had been reversibly deposited onto the silica surface.

Similarly, the dissipation change ($\Delta D$) occurred as soon as the samples solution made contact with the silica surface. There was a sharp increase of $\Delta D$ for both NCC and *P. flu* CHA0 supplemented with NCC from 0 to $0.75 \times 10^{-6}$ and kept stable till rinsing with background solution. A final $\Delta D$ of around $0.15 \times 10^{-6}$ for both NCC and *P. flu* CHA0 supplemented with NCC was achieved. With the adsorption of *P. flu* CHA0, the dissipation increased smoothly and decreased slightly upon rinsing with background solution. The final $\Delta D$ of *P. flu* CHA0 was around $0.5 \times 10^{-6}$.

Figure 4B:
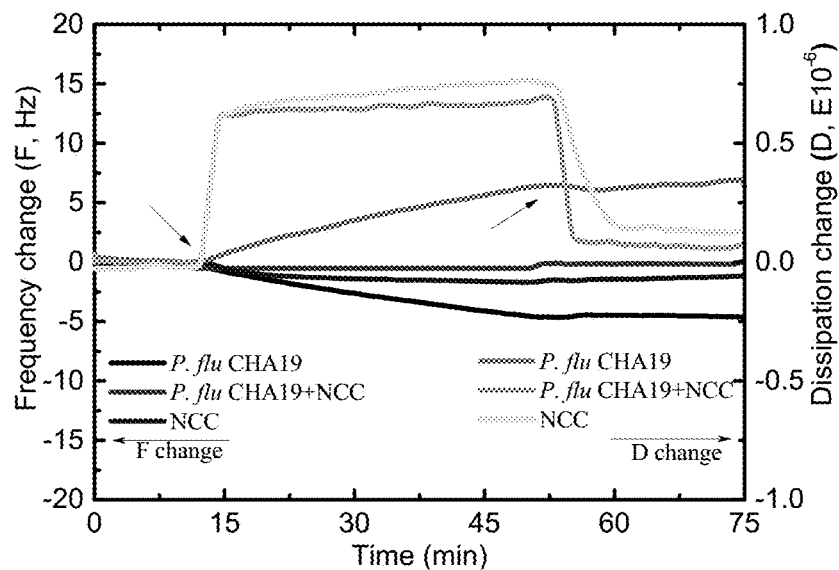

The adsorption of *P. flu* CHA19-WS achieved a final frequency shift ($\Delta F$) up to around 5 Hz, and only desorbed slightly upon rinsing with background solution. Consistent with the static adhesion results (FIG. 3), *P. flu* CHA19-WS (FIG. 4B) also showed a slightly higher adhesion capabilities than that of *P. flu* CHA0 (FIG. 4A) under hydrodynamic flow conditions. $\Delta F$ of the *P. flu* CHA19-WS supplemented with NCC was around 0.2 Hz and decreased to around 0 Hz when rinsing with background solution, indicating few *P. flu* CHA19-WS cells adsorbed onto the silica surface and the adsorption was loosely.

With the adsorption of *P. flu* CHA19-WS, the dissipation increased smoothly and decreased slightly upon rinsing with background solution, a final $\Delta D$ of about $0.35 \times 10^{-6}$ was achieved by *P. flu* CHA19-WS adsorption. There was a sharp increase of $\Delta D$ for *P. flu* CHA19-WS supplemented with NCC from 0 to $0.65 \times 10^{-6}$ and kept stable till rinsing with background solution. Upon rinsing with background solution, $\Delta D$ decreased to about 0.

Figure 4C:
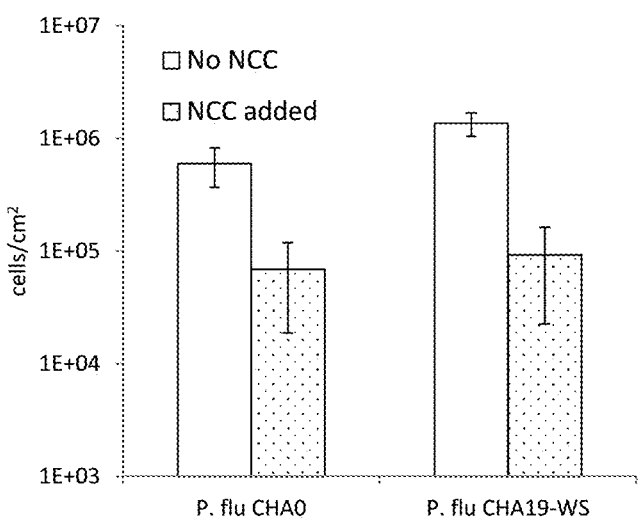

Microscopy images of the silica surfaces were captured after the QCM-D adhesion experiments to quantify the adhered cell numbers, and the cell density on silica surfaces was calculated (FIG. 4C) based on the microscopy images. As shown in FIG. 4C, adhesion of *P. flu* CHA0 (~$5.96 \times 10^5$ cells/cm$^2$) onto silica surfaces was significantly (p<0.05) inhibited by NCC (~$6.87 \times 10^4$ cells/cm$^2$, or ~88.5% inhibition), which was consistent with the *P. flu* CHA0 QCM-D adhesion results. The cell density of *P. flu* CHA19-WS on silica surface (~$1.36 \times 10^6$ cells/cm$^2$) was higher than that of *P. flu* CHA0 (~$5.96 \times 10^5$ cells/cm$^2$), which is consistent with the static adhesion results (FIG. 3). With the presence of NCC, adsorption of *P. flu* CHA19-WS was also significantly (p<0.05) hindered (to around $9.25 \times 10^4$ cells/cm$^2$, or ~93.2% inhibition) as per the microscopic observations (FIG. 4C), although the final ΔF of the *P. flu* CHA19-WS supplemented with NCC was about 0 in QCM-D experiments (FIG. 4B), which may be associated with the presence of EPS and surface hydrophobicity that have been reported to lead to the reduced ΔF in QCM-D results. Therefore, direct microscopy can be useful to support the frequency shift results in QCM-D bacterial adhesion studies.

2.3.3 Overall Impact of NCC on Bacterial Adhesion.

Significant reduction in bacterial adhesion on solid surfaces was observed in both static and dynamic experiments, and explanations of this observation are discussed below.

Firstly, bacterial flocs were formed in the presence of NCC. Based on the dimensions and flow rates employed in the QCM-D flow cell, the Pe number was estimated to be 0.001, indicating that the bacteria within the QCM-D system effectively experienced the diffusion-dominated flow regime. The larger sized bacterial aggregates formed in the presence of NCC have a lower diffusion coefficient than do single bacterial cells and hence will experience reduced convective-diffusive transport to the silica surface, resulting in lower deposition to the silica surface. A similar behavior was observed for the deposition of fullerene nanoparticles onto silica surfaces.

Secondly, it is known that increasing colloid size can lead to the increased fluid drag force, leading to the greater detachment rate. Thus secondary minimum-associated particles would be subject to fluid drag along the solid surface under hydrodynamic flow conditions and would be swept from the system. This expectation was confirmed by our QCM-D bacterial adhesion results (FIG. 4C) where the larger microbial aggregates deposited less onto the silica surface.

Thirdly, adsorption of NCC onto silica surfaces can reduce the deposition of bacterial cells and enhance the reentrainment of deposited bacterial cells on the surface. This affect may arise from additional electrostatic and steric contributions to the repulsive interaction energy, due to the adsorption of negatively charged NCC particles onto silica surfaces. Accordingly, NCC may be adsorbed onto the silica surface resulting in the higher negative zeta potential (~36.3±0.15 my and −42.3±1.07 my for silica surface and NCC respectively). Single bacterial cell adhesion was then hindered due to the enhanced repulsive forces between the bacterial cells and the silica surface.

Lastly, another additional reason for the reduction of bacterial adhesion in the presence of NCC may be a change in EPS conformation due to the presence of NCC suspended among the EPS, for example leading, as in this case, to more rigid polymers. This rigidity minimizes the ability of the polymers to reconform to and interact directly with the solid surface.

2.4. Classic DLVO Interactions.

Figure 5:
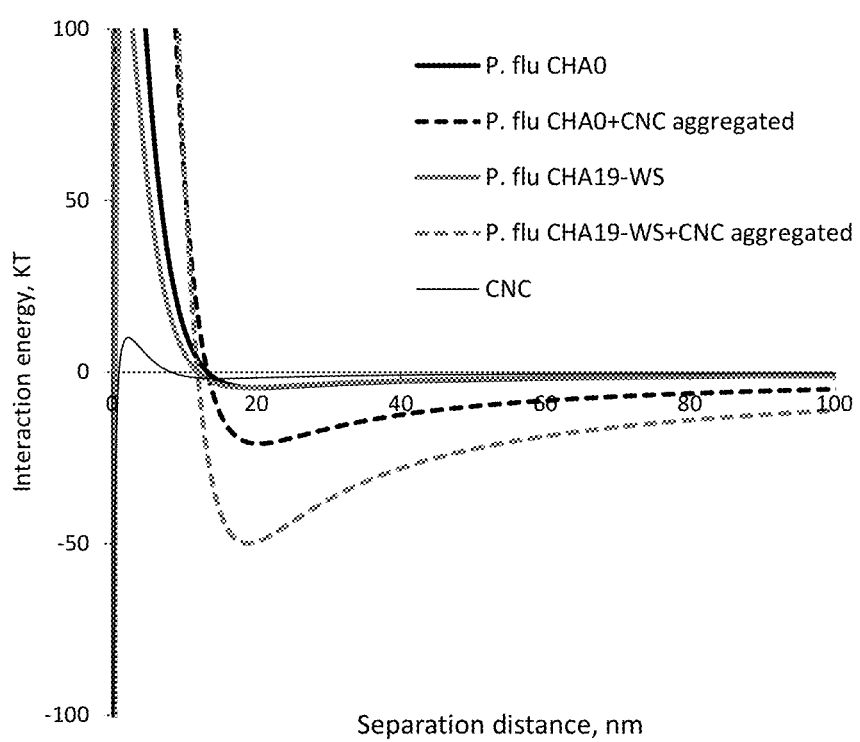
FIG. 5. Theoretical DLVO interaction energies between bacteria and silica (glass) surface with and without NCC, and DLVO interaction energies between CNC particles and the silica surface.

The experimentally measured equivalent radii and zeta potential values were used in the subsequent DLVO interaction energy calculations (Table 2). The primary energy minimum ($\Phi_{1min}$), the primary energy barrier ($\Phi_{max}$), and the secondary energy minimum ($\Phi_{2min}$) are presented in Table 2. The DLVO energy profile is depicted in FIG. 5. The negative Φ at primary energy minimum or secondary energy minimum indicates attractive forces that contribute to colloidal attachment whereas the positive Φ suggests a repulsive force promoting colloidal stability or mobility. Although a much idealized DLVO approach was applied by assuming bacterial cells and NCC particles as smooth spheres, the energy calculations can be considered to capture the qualitative trends of the samples.

TABLE 2

Key parameters used in DLVO calculations and interaction energies as calculated by DLVO theory.

| Sample | Size[a] (μm) DLS | Equivalent Radii | Zeta potential of bacteria (mv) | $\Phi_{1min}$[b] (kT) | $\Phi_{max}$[c] (kT) | $\Phi_{2min}$[d] (kT) |
|---|---|---|---|---|---|---|
| *P. flu* CHA0 | 1.76 ± 0.07 | 0.44 | −18.78 ± 1.31 | −860 | 202 | −4.6 |
| *P. flu* CHA0 + NCC | N/A | 2.0 | −18.78 ± 1.31 | −3907 | 920 | −20.9 |
| *P. flu* CHA19-WS | 1.44 ± 0.03 | 0.41 | −16.22 ± 0.89 | −847 | 118 | −4.6 |
| *P. flu* CHA19-WS + NCC | N/A | 4.5 | −16.22 ± 0.89 | −9293 | 1299 | −50 |
| NCC | 0.114 ± 0.002 | 0.0046 | −42.30 ± 1.07 | −42.1 | 3.8 | −0.25 |

[a]The average particle hydrodynamic size, determined by DLS.
Note:
aggregates size of *P. flu* CHA0, and *P. flu* CHA19-WS after addition of NCC was determined by microscopy.
[b]The depth of the primary energy minimum, calculated by DLVO theory.
[c]The height of the primary energy barrier, calculated by DLVO theory.
[d]The depth of the secondary energy minimum, calculated by DLVO theory.

FIG. 5 shows the energy sum of the electrostatic and van der Waals interactions, both of which decay with separation distance. Without NCC, the strong positive repulsive energy barriers of *P. flu* CHA0 (202 kT) and *P. flu* CHA19-WS (118 kT) to the silica surface interactions indicate that the adhesion of both cell types on the silica surface was unfavorable. Of note, the secondary minima of both bacterial strain were around −4.6 kT, which is higher than the average thermal energy of the Brownian particles themselves (~1.5 kT). Thus deposition in secondary minima for both strains was not negligible, which was confirmed by the bacterial adhesion results under both static (FIG. 3) and hydrodynamic flow (FIGS. 4A and 4C) conditions. Additionally, the depths of both secondary minima were close to each other, indicating that the secondary minimum deposition could not explain the observed difference in adhesion abilities of the two bacterial strains (FIGS. 3 and 4C). With the addition of NCC, DLVO predicted deep secondary minima (−50 kT for *P. flu* CHA19-WS and −20.9 kT for *P. flu* CHA0) for both bacterial cells to the silica surface indicating more cell deposition in secondary minima is expected, which is opposite to our adhesion results.

Figure 6:
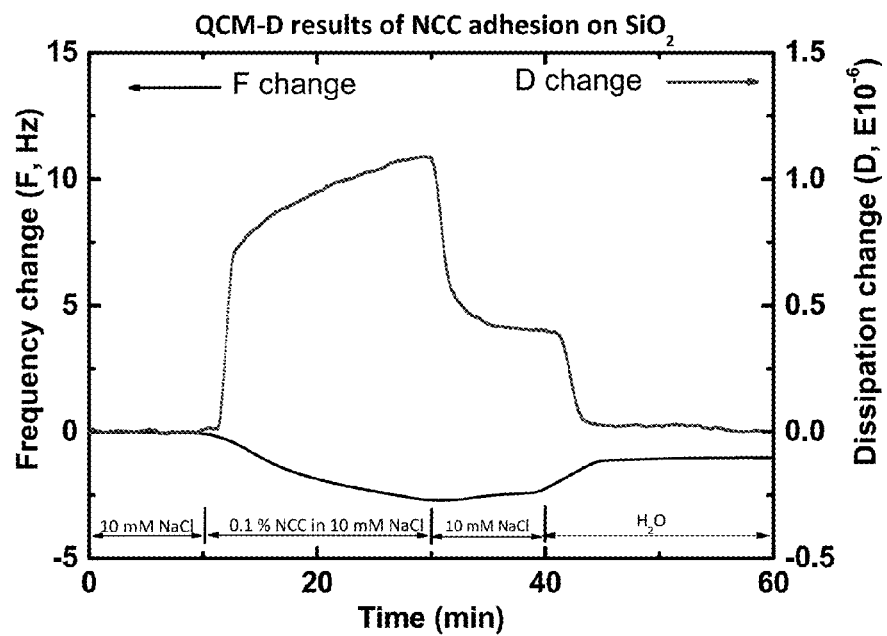
FIG. 6. QCM-D study on NCC adsorption onto silica surface (F change, bottom line; D change, top line).

In the case of NCC particles only, a positive energy barrier was predicted which was 3.8 kT. NCC may interact with the silica surface due to the presence of the reversible secondary minimum (−0.25 kT) at a small separation distance (around 15 nm). Our QCM-D study showed that previously deposited NCC was partially removed after ultrapure water injection (FIG. 6), indicating that the secondary minimum was likely involved in the NCC deposition onto the silica surface.

Calculating classic DLVO interactions failed to explain the bacterial adhesion behavior in this study, indicating that other interactions present between bacteria and silica surface must be responsible. In the current flow system, bacterial cells interacting with a silica surface may also experience steric, hydration, and hydrodynamic forces when approaching the surface, therefore, the adhesion behavior may be altered. Surface charge heterogeneity and surface roughness of both bacterial and silica surfaces may represent other explanations for the deviation of the observed adhesion from predicted DLVO curves. In the presence of water, silica surfaces may become hydroxylated, with the surface acquiring charge through the ionization of hydroxyl groups. Bacterial adhesion to the silica surface due to surface charge heterogeneity was not considered in the classic DLVO interaction calculations, where the zeta potentials employed for both the bacterial suspensions and silica surfaces represented the average electrokinetic charges of the heterogeneous bacterial and silica surfaces. Furthermore, the zeta potential of the silica surface may have changed due to the deposition of NCC. However, the distribution of NCC on the silica surface has not been definitively evaluated, and the reference zeta potential values used in the classic DLVO interaction calculations are likely not accurate.

3. Experimental Details.

Glass Slides Cleaning Protocol.

Prior to each experiment, the slide pieces (1 cm×1 cm) were thoroughly rinsed with deionized (DI) water to remove visible impurities (large particles). Subsequently, the slides were immersed in 1N HCl and sonicated for 10 minutes to remove grease. After sonication, the slides were rinsed with sterilized ultrapure water, 70% ethanol, and sterilized ultrapure water successively. Finally, the drying process was achieved in a biosafety cabinet (CLASS II Type A2, Microzone Cor., Canada). The clean slides were reserved as bare slides used in the bacterial aggregation and adhesion experiments. See Hwang et al., *Biofouling* 2012, 28, 525-538, for additional technical details.

Zeta Potential Measurements of Glass Slides.

To determine the surface charge of bare glass slide surfaces, silicon dioxide particles (approx. 99%; particle size 0.5-10 μm with 80% being between 1-5 μm. Sigma-Aldrich) were used. Zeta potential of silicon dioxide particles was measured in 10 mM NaCl solution using a Malvern Zetasizer Nano-ZS (Model: ZEN3600, Malvern Instruments Ltd, Worcestershire, UK) at 25° C. Zeta potential is reported to be −36.3±0.15 my in this study.

Depletion Potential Calculations.

The depletion potential W for the same colloidal spheres with the radius R in the presence of rod-like particles is given as:

$$W(h) = -\frac{2}{3}k_B T \phi_r \frac{L}{D} \frac{R}{D} \left(1 - \frac{h}{L}\right)^3 \qquad \text{Equation 3}$$

where $k_B$ is the Boltzmann constant, T is the absolute temperature, L is the length, D is the diameter, $\phi_r$ is the volume fraction of rod-like particles (NCC particles here), R is the diameter and h is the surface-to-surface distance of large spherical colloidal particles (bacterial cells here). One can estimate the needed depletant concentration if the attraction energy of −3 $k_B T$ is assumed sufficient to induce the phase separation of large particles. See Lekkerkerker and Tuinier, Colloids and Depletion Interaction; *Springer* 2011, p. 100, for additional technical details.

Study Parameters:
L=100 nm;
D=10 nm;
R=440 and 410 nm (Equivalent Radii) for *P. flu* CHA0 and *P. flu* CHA19-WS cells, respectively;
$\phi_r$=5×10$^{-3}$ mL/mL.

According to Equation 3, the depletion potential W(h) was −1.5 $k_B T$, which is less than −3 $k_B T$. Therefore, the depletion aggregation was unfavorable in the current study.

Example 2. Role of Solution Chemistry on the Aggregation and Initial Adhesion of *Escherichia coli*

The aggregation and initial adhesion (to silica surfaces) of bacteria are affected greatly by solution chemistry, including pH, ionic strength (IS). The role of solution chemistry on the aggregation and deposition of *E. coli* K12 on silica surfaces were investigated in NaCl solutions under electrostatically unfavorable attachment conditions varying in pH and IS, and in the absence and presence of cellulose nanocrystals (CNC). pH and IS were found to have a marked effect on bacterial aggregation and deposition (to silica surfaces) in the absence and presence of CNC. Generally, with the presence of CNC, bacterial aggregation was enhanced by increasing pH and increasing IS. Lower deposition rates observed at higher IS and higher pH were attributed to aggregation of bacteria resulting in decreased convective-diffusive transport to the silica surface. Calculating classic DLVO interactions failed to fully explain the bacterial adhesion behavior in this study, indicating that other interactions present between bacteria and silica surface must be responsible. Adjusting the pH and IS of a CNC hydrogel composition used to coat a surface, such as a catheter or other medical device, can therefore reduce or prevent bacterial adhesion and can increase aggregation, thereby reducing the opportunity for bacteria to infect a host, such as a patient being treated with a medical device.

1. Introduction.

The electrostatic repulsion between bacterial cells as well as cells and support surface can be modulated or controlled by pH. The surface of the bacterial cells studied in this example was less negatively charged at lower pH due to the deprotonation decrease of various chemical groups, such as carboxyl ($CO_2^-$) groups, resulting in a decreased electrostatic repulsion and enhanced the adhesion between the bacteria and the support.

Example 1 showed that rod-shaped CNC particles, even at low concentrations (relative to the model prediction), are very effective in agglomerating gram-negative EPS producing bacteria *Pseudomonas aeruginosa* PAO1 through a depletion mechanism. However, it was unclear how CNC-induced bacterial aggregation and adhesion might vary depending on the solution chemistries of aqueous or physiological environments. This example evaluates the effect of solution chemistry on the aggregation and adhesion (e.g., to silica surfaces) of bacterial cells (e.g., *E. coli* K12) with and without the presence of CNC. The aggregation of bacteria in the absence and presence of CNC was assessed by microscopy and the deposition of bacteria on solid surfaces in the absence and presence of CNC was determined using a batch method. Microscopy was used to quantify cell deposition.

2. Material and Methods.

2.1. Culturing and characterization of bacterial cells. Gram-negative strain of *Escherichia coli* K12, was selected as the model bacterial culture in this study to perform the bacterial aggregation and adhesion experiments. For each experiment, the stored strain was streaked onto an Luria-Bertani (LB) agar plate and then incubated at 37° C. overnight. A single colony from the plate was then transferred into 50 mL of LB broth and grown in a shaker incubator at 150 rpm and 37° C. for 16 hours. Thereafter, stationary-phase bacterial cells were harvested by centrifugation at 3000 g and 4° C. for 10 minutes. The pellets were resuspended in a desired NaCl solution (varying in different pH and IS), prepared with reagent grade salt (Fisher Scientific Inc., U.S.) and Milli-Q water (18.2 MΩ, Millipore, Mississauga, ON, Canada), and sterilized by autoclave before use. The centrifugation and re-suspension procedures were repeated two additional times to remove traces of growth media and suspended EPS from the solutions. A final cell density of $1.0\times10^8$ cells·mL$^{-1}$ was obtained by measuring the optical density (OD) at 600 nm with a UV spectrophotometer (Varian Inc., U.S.). Scanning electron microscopy (SEM) was employed to characterize the morphology of bacterial cells. The zeta potential of *E. coli* K12 cells versus pH and IS was determined by dynamic light scattering (DLS) spectrophotometer (Malvern Zetasizer Nano ZS. Model: ZEN3600, Malvern Instruments, UK) at 25° C. The average hydrodynamic size of *E. coli* K12 cells was also determined by DLS. Bacterial suspensions were prepared in NaCl solution of interest and each measurement was repeated with at least three different samples.

2.2. CNC suspension preparation and characterization. A stock suspension of 1.0% (wt.) CNC in NaCl solution with different IS and pH was prepared following the protocol of Example 1. Zeta potential of the CNC particles as a function of IS and pH was assessed by DLS measurements at 25° C. CNC suspensions were prepared in NaCl solution of interest and each measurement was repeated with at least three different samples.

2.3. Bacterial aggregation experiment. In the aggregation experiment, 1 mL 1.0% (wt.) CNC suspension was added to 1 mL of the bacterial suspensions (with pH adjustments) to achieve a volume fraction of $5\times10^{-3}$ mL·mL$^{-1}$. Treatment controls without CNC were also prepared. The whole system was incubated statically at 24° C. for 30 minutes and stained with SYTO® 9 green fluorescent nucleic acid dye (Life Technologies) for another 15 minutes before bacterial cells were dropped on clean microscopy glass slides to facilitate fluorescent microscopic observations. Microscopic visualization of the slides was carried out under fluorescent light using an Axio Imager M2 microscope (Carl Zeiss, Germany) with a Zeiss LD Plan-NEOFLUAR 40× objective. At least fifty images of randomly chosen areas of each slide were taken. The images were analyzed using AxioVision 4.8, the size (diameter) of each bacterial aggregates on each image was measured and then averaged to get the average size before and after CNC treatment. These experiments were conducted in triplicate in at least five independent experiments.

2.4. Bacterial initial adhesion on silica surface. For each adhesion experiment, fresh *E. coli* K12 bacterial suspensions ($1.0\times10^8$ cells·mL$^{-1}$ in NaCl solutions with various IS) were prepared as described in section 2.1 above. One mL was distributed in each well of a 24-well plate (Corning Inc., U.S.) and then 1 mL of 1.0% (wt.) CNC suspension was added to each well, followed by pH adjustments with 1M NaOH/1N HCl. The cleaned glass slides (diameter 1.2 cm, Fisher Scientific Inc., U.S.) were completely submerged in the bacterial suspension for 30 minutes at 24° C. in a static state to allow the bacteria to attach to the surfaces. Then the bacterial suspension was removed and the glass slides were carefully washed three times with NaCl solution to remove loosely attached bacteria. To observe the differences before and after CNC treatment, the visualization and quantification of attached cells on slides were completed by fluorescent microscopy.

Briefly, after each adhesion test, the bacteria coated slides were placed on clean microscope slides and stained with SYTO® 9 green fluorescent nucleic acid dye for 15 minutes. Thereafter, the fluorescent light and a 40× objective were used to take a minimum of fifty randomly chosen fields of view of each slide. The size of each image was approximately $3.76\times10^{-4}$ cm$^2$. The number of bacteria in each image was obtained through counting five areas (4 corners plus the center) of the image, then averaged. Bacterial adhesion experiments were conducted in triplicate in at least five independent experiments. The variance of bacterial adhesion was analyzed with a one-way analysis of variance (ANOVA) and was reported as p-values. P-values of less than 0.05 indicate significant differences.

2.5. DLVO interaction energy calculations. The initial adhesion of bacteria to solid substratum in aquatic systems is generally considered to be similar to the deposition of colloidal particles. Thus, classic DLVO theory of colloid stability, simulating bacteria-surface interactions, can generally be applied to explain bacterial adhesion behaviors.

3. Results and Discussion.

Figure 7:
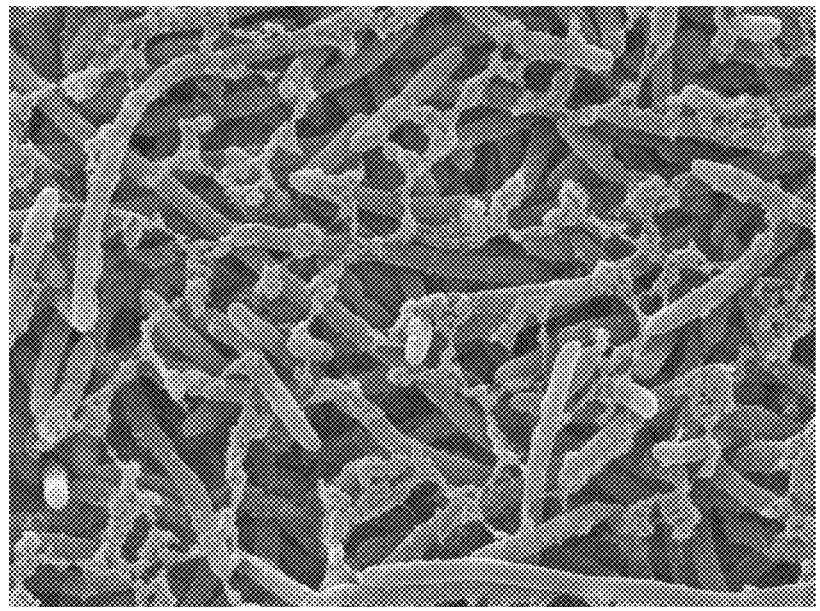
FIG. 7. Representative SEM micrographs of E. coli K12.

3.1. Characterization of bacterial cells and CNC particles. As shown in FIG. 7, *E. coli* K12 cells were rod-shaped and equipped with thread-like EPS appendages. Based on DLS measurements, the average hydrodynamic size of *E. coli* K12 was 4.8±0.5 μm which was taken as the cell length. The resulting equivalent spherical radius of one *E. coli* K12 cell was 0.6 μm which was used in DLVO interaction energy calculations.

Zeta potential values of CNC and *E. coli* K12 as a function of pH and IS of the NaCl solution were calculated. Both CNC and *E. coli* K12 exhibited negatively charged surfaces over the tested pH and IS range. Both pH and IS play significant roles on the zeta potential changes of *E. coli* K12.

At 10 mM, the zeta potential of the *E. coli* K12 cells became more negative when pH of the NaCl solution increased from 2.7 to 7.2. The surface of the cells was more negatively charged at higher pH due to the deprotonation increase of various chemical groups, such as carboxyl (—COOH), phosphate ($PO_4^{2-}$). At pH 7.2, zeta potential of *E. coli* K12 cells became less negative when IS of NaCl solution increased from 1 mM to 50 mM. The IS of the medium is an important factor affecting the electrostatic interactions. Based on the EDL theory, an increase of IS will suppress the electric double layer (EDL) resulting in a decrease of the zeta potential of a colloidal particle. *E. coli* K12 are Gram-negative bacteria, their outer membrane is high in lipid and low in peptidoglycan relative to Gram-positive bacteria, therefore, the solution chemistry has more remarkable influence on their cell properties (e.g. size and charge).

Further, the zeta potential of CNC particles in 10 mM NaCl remained relatively constant at about −43 mV with pH increasing from 2.4 to 7.2, indicating a stable CNC suspension varying in the pH range tested in this study. With the increase of the IS, the zeta potential of the CNC particles became less negative at pH 7.2, which can also be explained by the EDL theory. It was also observed that, with increasing IS, the CNC suspension destabilized. The average CNC particle size increased from about 100 nm to 250 nm with IS increasing from 1 mM to 50 mM.

Figure 8:
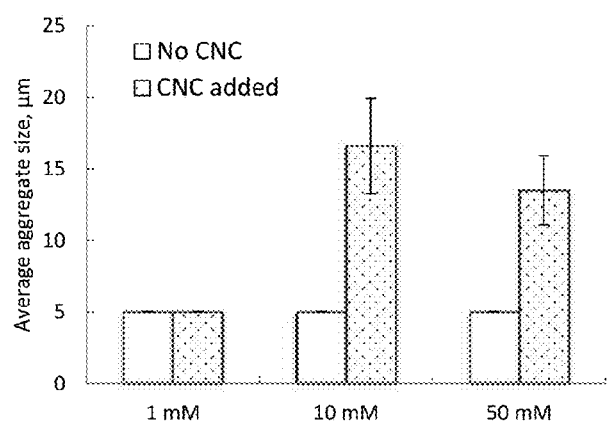
FIG. 8. Impact of IS on E. coli K12 aggregation and adhesion with and without CNC. (A) Average aggregates size; and (B) average adhesion cell density (error bars represent one standard deviation) (pH=7.2).
Figure 8:
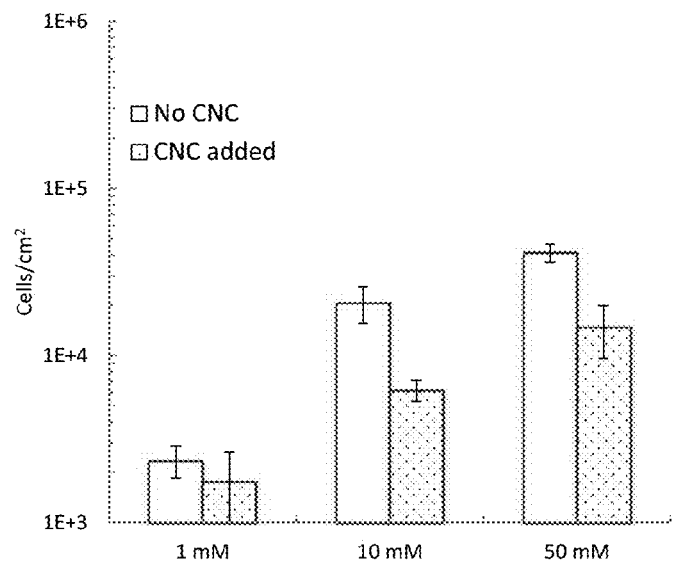

3.2. Impact of IS on bacterial aggregation and initial bacterial adhesion. As shown in FIG. 8A, without CNC, E. coli K12 suspension were well dispersed, flocculate free at all three IS conditions (the average radius of one E. coli K12 cell was about 5 μm). With the addition of CNC, E. coli K12 at 10 mM NaCl solution showed very significant aggregation and formed dense bacterial clusters with an average size (diameter) of about 17 μm (FIG. 8A), indicating CNC induced aggregation of E. coli K12 suspension.

Several large but loose E. coli K12 clusters also emerged at 50 mM NaCl solution. CNC induced depletion of E. coli K12 suspension might be the dominant reason for the bacterial aggregation under this condition. At 50 mM NaCl solution, both E. coli K12 cells and CNC particles became less negatively charged and unstable, thus CNC induced less aggregation of E. coli K12 cells. At 1 mM NaCl solution, no E. coli K12 clusters were observed under microscopy (FIG. 8A). More negative zeta potential of both E. coli K12 cells and CNC particles at 1 mM indicates a stable system because of the electrostatic repulsion between CNC particles and bacterial cells as well as cells and cells increased. Although bacterial cells can spontaneously form agglomerates, without CNC application agglomerates were unlikely to form.

Our results showed that CNC particles induce bacterial aggregation mainly through depletion interactions. Based on the depletion mechanism, the addition of repulsive CNC particles into a dispersion of larger colloidal bacterial cells destabilizes the system.

One can estimate the needed depletant concentration if the attraction energy of $-3$ $k_BT$ is assumed sufficient to induce the phase separation of large particles. The depletion potential W(h) was $-2.06$ $k_BT$, which is less than $-3$ $k_BT$. Therefore, the depletion aggregation was unfavorable in the current study. Explanations for the observed deviation of the aggregation from predicted depletion potentials include the following.

First, the equation used in the depletion potential calculations is ideal for large spherical particles in the presence of small, rod-shaped particles, whereas the bacterial cells in the current study were cylindrically shaped. Second, the deviation may be explained by the presence of bacterial EPS, which could impose polymer-mediated steric interactions such as polymer bridging that were not considered in the predicted depletion potentials. EPS surrounding the bacterial cells can trigger a depletion interaction among the bacterial cells. Repulsive interactions between like-charged bacterial cells can lead to depletion, whereas the presence of EPS can impose polymer bridging. As polymer induced forces are sensitive to the IS of the solution, the impact of polymer bridging on bacterial adhesion in the presence of CNC under different IS conditions should be investigated.

FIG. 8B illustrates the enumeration of the cell density of E. coli K12 deposited on glass slides at different IS with and without CNC, determined from fluorescent microscopy observations. In the absence of CNC, bacterial adhesion capacity increased with the increase of IS, which is in agreement with the EDL theory. An increase of IS will suppress the EDL resulting in a decrease in the zeta potential (less negative) of bacterial cell surfaces and solid surfaces; thereafter, the repulsion between cells and the surface decreased which enhanced the cells adhesion capacity. After CNC addition, bacterial adhesion was inhibited at high IS conditions (i.e., 10 mM and 50 mM). Among the three IS conditions texted in this study, deposition of E. coli K12 on glass slides was the most significantly inhibited (p=0.008) at 10 mM, and achieved about 0.52 log-unit reduction (~70%) in cell density; at 50 mM, deposition of E. coli K12 on glass slides was also significantly (p=0.03) inhibited by 0.44 log-unit (~64%); while CNC did not significantly (p>0.05) reduce the deposition of E. coli K12 on glass slides 1 mM. This might be associated with the fact that the larger sized bacterial aggregates formed in the presence of CNC at 10 mM have a lower diffusion coefficient than do single bacterial cells and hence will experience reduced convective-diffusive transport to the silica surface, resulting in lower deposition to the surface. The sensitivity of particle deposition rate to solution IS decreases as the degree of surface charge heterogeneity increases. In the current study, the deposition of CNC particles on silica surface may increase the silica surface charge heterogeneity, and consequently decrease bacterial deposition rate.

Figure 9:
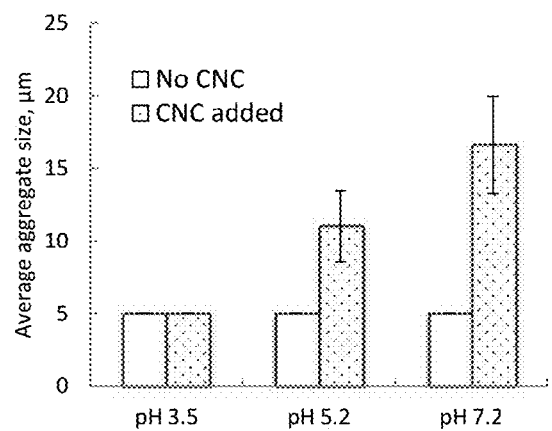
FIG. 9. Impact of pH on bacterial aggregation and adhesion with and without CNC. (A) Average aggregates size; and (B) average adhesion cell density (error bars represent one standard deviation) (IS=10 mM NaCl).
Figure 9:
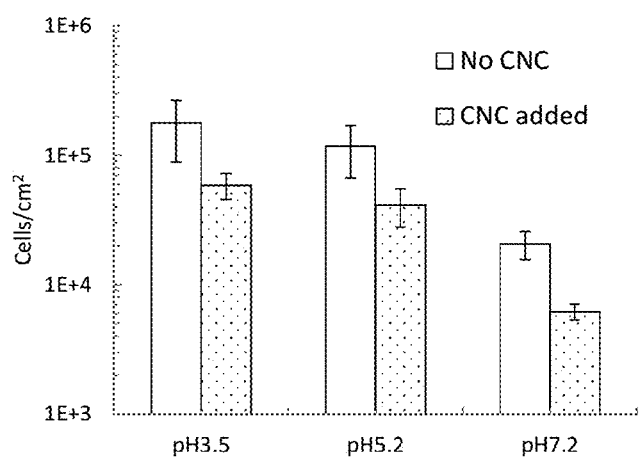

3.3. Impact of pH on bacterial aggregation and initial bacterial adhesion. A relatively mild pH range from 3.5 to 7.2 was selected in the current study. FIG. 9 shows E. coli K12 aggregation (FIG. 9A) and adhesion (FIG. 9B) at different pH (at 10 mM). Without CNC, E. coli K12 suspension was flocculate free at all three pH conditions (pH 3.5, 5.2, and 7.2) (FIG. 9A). After addition of CNC, E. coli K12 tended to aggregate to an average size of about 17 μm at pH 7.2, but not at pH 3.5. Smaller aggregates with an average size of about 11 μm were also observed at pH 5.2 (FIG. 9A).

FIG. 9B illustrates E. coli K12 cell deposited on silica surface at different pH (at 10 mM) with and without CNC. In the absence of CNC, bacterial adhesion capacity decreased with the increase of pH. After CNC addition, deposition of E. coli K12 on silica surface was significantly (p=0.008) inhibited (0.52 log-unit reduction) at pH 7.2; while CNC did not significantly inhibit the deposition at pH 3.5 (p=0.08) and pH 5.2 (p=0.06). The adhesion results correlates with the aggregation results (FIG. 9A), in which CNC induced more significant aggregation of E. coli at higher pH than at lower pH. This effect is likely a result of reduced convective-diffusive transport to the silica surface due to the larger sized bacterial aggregates formed in the presence of CNC at higher pH.

Figure 10:
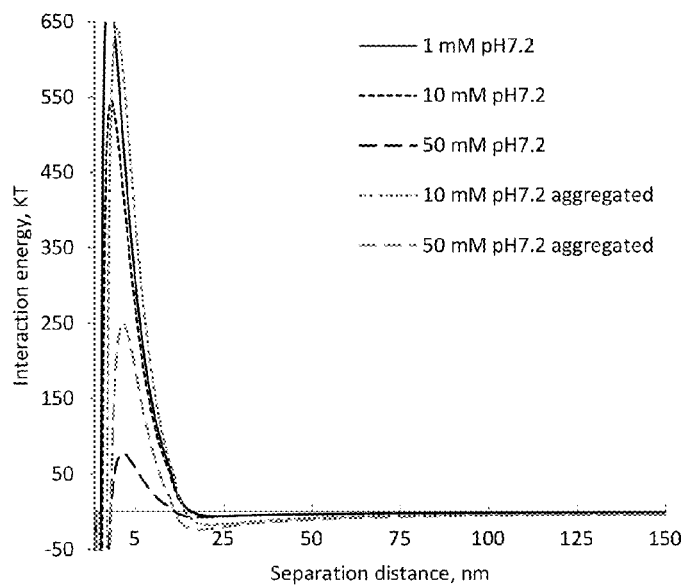
FIG. 10. Theoretical DLVO interaction energy profiles between bacteria and glass surface with and without CNC.
Figure 10:
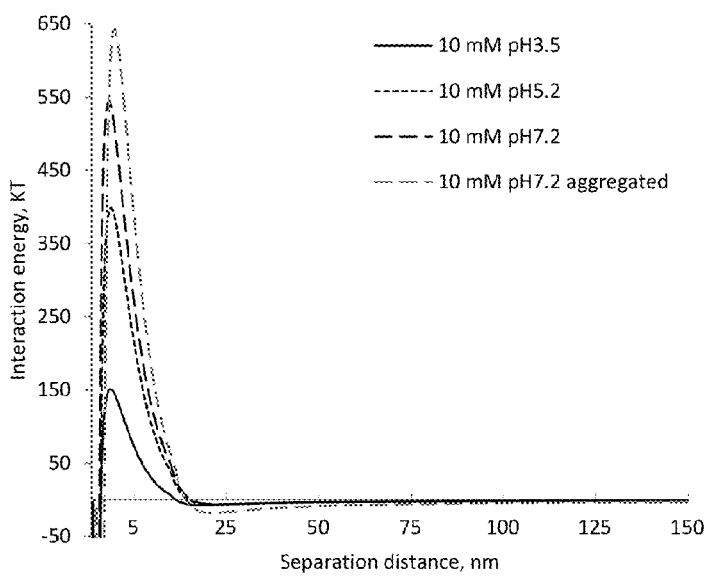

3.4. Application of classic DLVO theory. The experimentally measured equivalent radii and zeta potential values were used in subsequent DLVO interaction energy calculations. The zeta potential of the glass slides was determined by measuring the zeta potential of silicon dioxide particles. The DLVO energy profile is depicted in FIG. 10. The negative Φ at primary energy minimum or secondary energy minimum indicates attractive forces that contribute to colloidal attachment whereas the positive Φ suggests a repulsive force promoting colloidal stability or mobility. Although a much idealized DLVO approach was applied by assuming bacterial cells and CNC particles as smooth spheres, and the distribution of surface charge is uniformly distributed on bacterial cells, CNC particles and silica surfaces, the energy calculations can be considered to capture the qualitative trends of the samples.

The energy sum of the electrostatic and van der Waals interactions at different IS (pH=7.2), and different pH (IS=10 mM) are shown in FIGS. 10A and 10B, respectively, both of which decay with separation distance. Without CNC, the strong positive repulsive energy barriers of E. coli K12 to silica surface (FIG. 10A) suggest that the adhesion of *E. coli* K12 to silica surface was unfavorable. Despite the presence of energy barriers, bacterial deposition onto overall like-charged silica surface was well demonstrated in FIG. 8B and FIG. 9B. Properties such as surface roughness, localized nanoscale patches of attractive surface charge, way be contributing factors. Those bacteria that are capable to overcome these energy barriers can fall into deep primary energy minima (could not be shown in FIG. 10) at close contact and attach to the surface irreversibly. Those are not able to overcome the energy barriers could be associated with the surface via secondary energy minima with no direct contact, thus the adhesion is reversible and very likely to leave the surface under any variation of conditions (such as solution chemistry).

FIG. 10A shows the energy profile of the impact of IS (pH=7.2) on bacterial initial adhesion. It can be observed that the depth of the secondary energy minimum and the height of the repulsive energy barriers increases and decreases, respectively, with increasing IS (FIG. 10A), which is expected based on EDL theory. Diffusion of bacteria over these energy barriers is highly unlikely. Thus, DLVO calculations indicate unfavorable attachment conditions for the primary minimum, but a potential for a weak association via the secondary minimum. Of note, the secondary minima of *E. coli* K12 at three different IS were around −6.0 kT (IS=1 mM), −6.1 kT (IS=10 mM), and −7.4 kT (IS=50 mM) respectively, which are all higher than the average thermal energy of the Brownian particles themselves (~1.5 kT). Thus deposition in secondary minima for *E. coli* K12 at the three tested IS was not negligible, which was confirmed by the bacterial adhesion results (FIG. 8B). With the addition of CNC, DLVO predicted deeper secondary minima (−17.7 kT and −24.0 kT for *E. coli* K12 at 10 mM and 50 mM, respectively) to the silica surface, compared to that without CNC (−6.1 kT and −7.4 kT for 10 mM and 50 mM, respectively), indicating higher affinity to silica surface and thus more cell deposition in secondary minima is expected after CNC addition, which is opposite to the adhesion results (FIG. 8B).

FIG. 10B shows the energy profile of the impact of pH (IS=10 mM) on bacterial initial adhesion. Without CNC, the energy barriers increased with the increasing of pH, indicating lower affinity to silica surface and thus less cell deposition in secondary minima at higher pH, which is consistent with the adhesion results (FIG. 9B). At pH 7.2, the height of energy barrier and the depth of secondary minimum increased and decreased with the addition of CNC, respectively, compared with no CNC. Thus deposition in the secondary minimum for *E. coli* K12 at pH 7.2 after addition of CNC was supposed to be promoted. However, the adhesion results shown in FIG. 9B indicates less deposition after CNC addition, probably due to CNC induced bacterial aggregation and the increased primary energy barrier.

Calculating classic DLVO interactions failed to fully explain the bacterial adhesion behavior described in this example, indicating that other interactions present between bacteria and silica surface must be responsible. DLVO theory assumes microbial cells to be inert particles, and the surfaces to be perfectly smooth which in reality do not exist. In the current static system, bacterial cells interacting with a silica surface may also experience steric, hydration, and specific interactions when approaching the surface, therefore, the adhesion behavior may be altered.

Surface charge heterogeneity and surface roughness of both bacterial and silica surfaces may represent additional explanations for the deviation of the observed adhesion from predicted DLVO curves. Surface charge heterogeneity and surface roughness may locally reduce or eliminate the energy barriers to deposition and create locally favorable conditions for colloid deposition. In the presence of water, silica surfaces may become hydroxylated, with the surface acquiring charge through the ionization of hydroxyl groups. However, bacterial adhesion to silica surface due to surface charge heterogeneity was not considered in the classic DLVO interaction calculations, where the zeta potentials employed for both the bacterial suspensions and silica surfaces represented the average electrokinetic charges of the heterogeneous bacterial and silica surfaces.

Thus, in the presence of CNC, bacterial aggregation was enhanced by increasing pH and increasing IS. Lower deposition rates were observed at higher IS and higher pH, which attributed to aggregation of bacteria resulting in decreased convective-diffusive transport to the silica surface. Calculating classic DLVO interactions failed to fully explain the bacterial adhesion behavior in this study, indicating that other interactions present between bacteria and silica surface must be responsible. Adjusting the pH and IS of a CNC composition can thus be used to coat a surface and reduce or prevent bacterial adhesion and increase aggregation, thereby reducing the opportunity for bacteria to infect a host.

Figure 11:
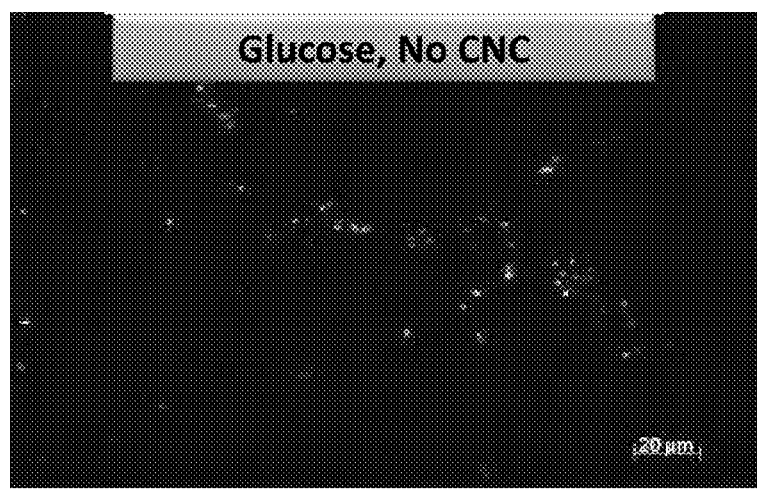
FIG. 11. Microscopic visualization of slides was carried out under fluorescent light using an Axio Imager M2 microscope (Carl Zeiss, Germany) with a Zeiss LD Plan-NEO-FLUAR 40× objective. A final Pseudomonas aeroginosa PAO1 cell density of $1.0 \times 10^8$ cells·mL$^{-1}$ was obtained by measuring the optical density (OD) at 600 nm with a UV spectrophotometer (Varian Inc., U.S.). One mL bacterial suspension+1 mL 2% (by wt.) CNC suspension+20 μL 1 g/L glucose or 1 g/L HA (final CNC concentration is 1% by wt.). All in 10 mM NaCl, pH=6.2. Images showing the initial low level of bacterial aggregations (A) in the presence of glucose without CNCs; (B) in the presence of glucose with CNCs; (C) in the presence of humic acid (HA) without CNCs; and (D) in the presence of humic acid with CNCs.
Figure 11:
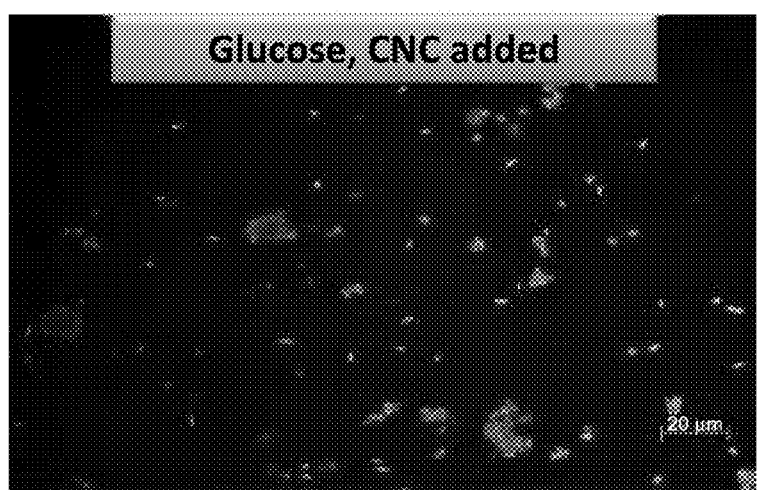
Figure 11:
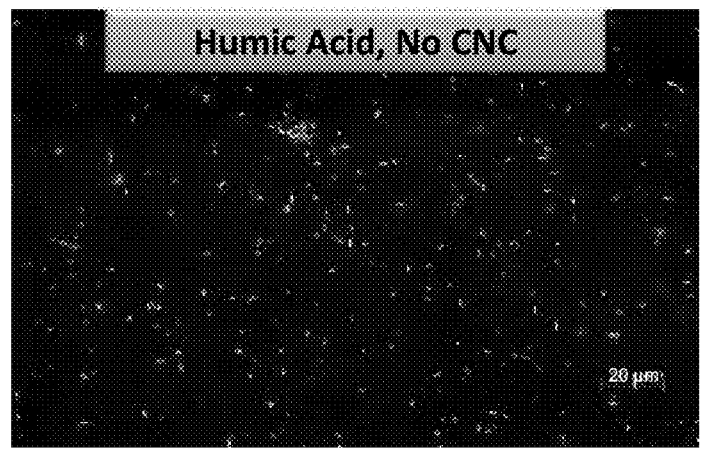
Figure 11:
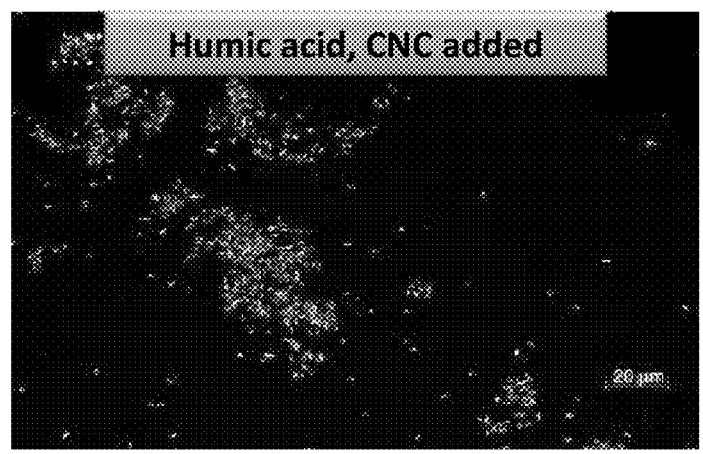
Figure 12:
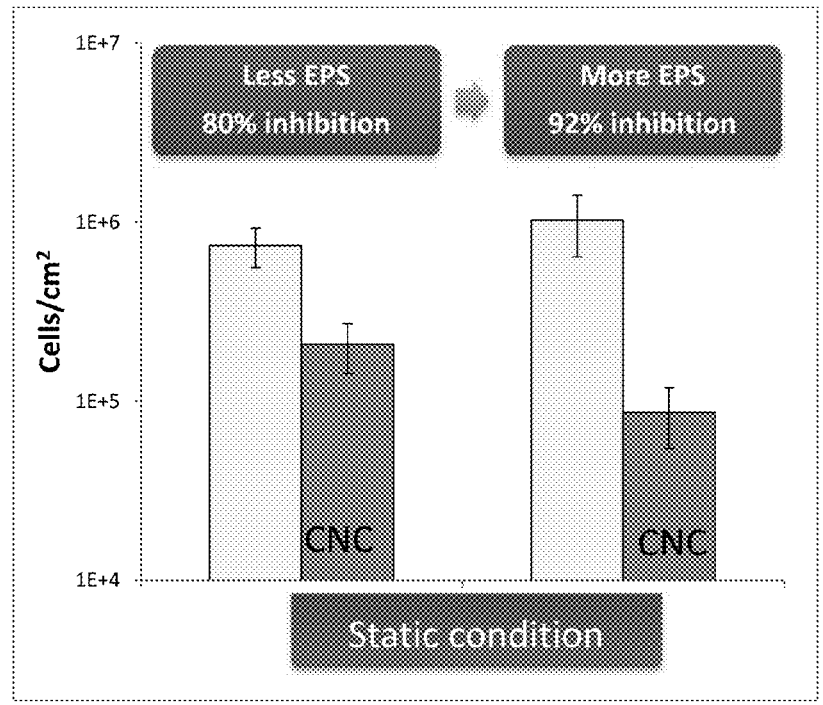
FIG. 12. Graphs showing reduction in Pseudomonas fluorescens bacterial adhesion under (A) static conditions and (B) hydrodynamic conditions, measured by analysis of cells/cm$^2$.
Figure 12:
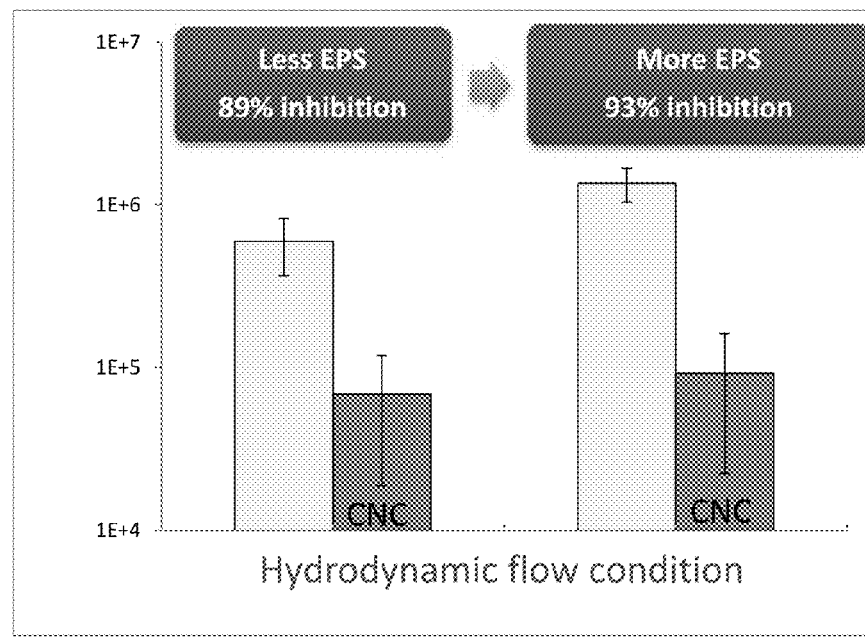

Example 3. Organic Compounds Improve CNC-Induced Aggregation and Reduce Bacterial Adhesion It was surprisingly discovered that certain organic compounds can be added to a CNC composition to increase the ability of CNC to aggregate bacteria and reduce or prevent biofilm formation. While humic acid and monosaccharides alone promoted only a minor amount of aggregation of bacterial cells, it was found that humic acid and monosaccharides such as glucose (e.g., at about 1 mg/mL) significantly improve bacterial aggregation in the presence of CNCs. As shown in FIG. 11, the addition of humic acid or glucose significantly increases the aggregation of bacteria by at least three-fold, typically 10-20 fold. Humic acid used was IHSS Suwannee River Humic Acid Standard II 2S101H, but a variety of humic acids can be effective. Also, the presence of organic additives with CNC reduces bacterial adhesion under both static and hydrodynamic flow conditions, as shown in FIG. 12. Thus, these organic additives can be used in combination with CNCs or in a CNC hydrogel to promote aggregation, reduce bacterial adhesion, and thereby reduce the occurrence of bacterial infections.

Example 4. CNC Hydrogels Reduce Bacterial Adhesion

Figure 13:
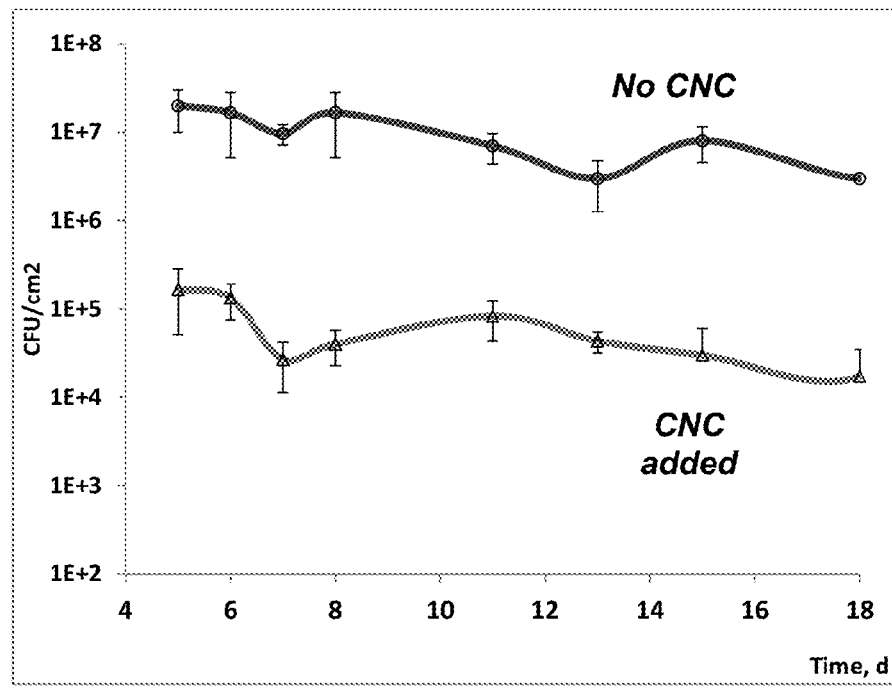
FIG. 13. CNC hydrogels significantly reduce bacterial adhesion and biofilm formation on silicone and Silvertouch catheters, measured by analysis of CFU/cm$^2$.
Figure 13:
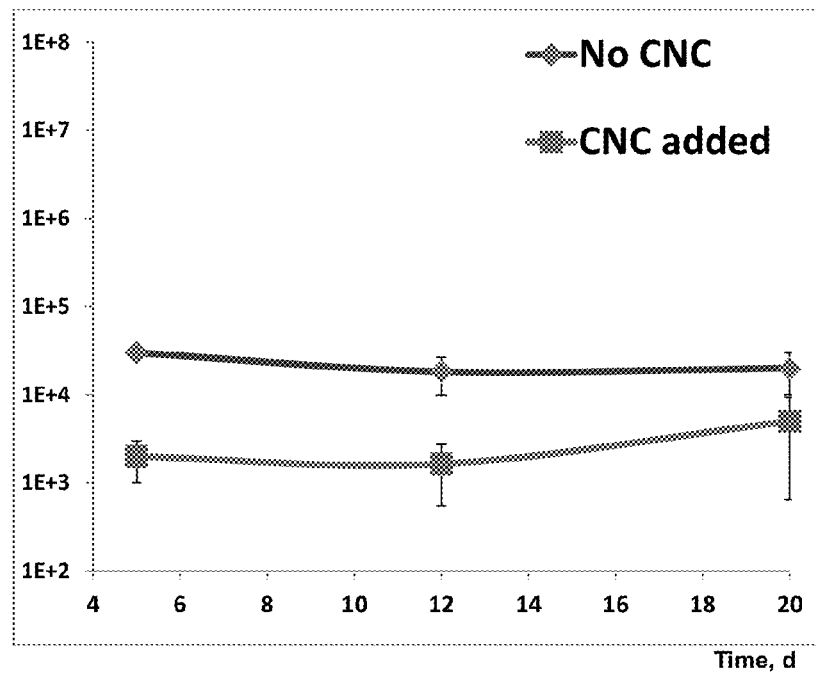

The presence of a CNC hydrogel on the surface of a catheter significantly reduces biofilm formation. Biofilm formation on catheters was reduced by 2-log units when the catheters were coated with a CNC hydrogel, as shown in FIG. 13. This biofilm reduction can be further increase by the addition of humic acid or monosaccharides, as described above. The experimental conditions for obtaining the data of FIG. 13 are as follows.

Flow rate=0.5 mL/min continuous flow;

$1 \times 10^6$-$1 \times 10^7$ CFU/mL *P. aeruginosa* PAO1 in synthetic urine solution;

For sampling, 3 cm of catheters was cut off and immersed in 2 mL 1% PBS buffer, followed by 10 minutes of sonication. Thereafter, heterotrophic plate counting was conducted to determine the cell density (cells/mL) in the buffer.

In terms of the aggregation effects, extracted bacterial EPS, glucose, and humic acids significantly promoted bacterial aggregation. The impact from alginate on the bacterial aggregation was not significant, i.e., the impact of CNC on the bacterial aggregation was not enhanced by alginate addition in the solution. Therefore, the identification of using saccharides and/or humic acid represents an additional improvement in techniques that can be used to reduce or prevent bacterial adhesion, thereby inhibiting or preventing the formation of biofilms, thus inhibiting or reducing the occurrence of bacterial infections in a patent that uses the hydrogel-coated catheters.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A catheter comprising a nanocrystalline cellulose (NCC) hydrogel coating for the inhibition of urinary tract infections, wherein the NCC hydrogel comprises NCC, a water-soluble polymer, and water, wherein the NCC hydrogel comprises about 1-20 wt. % NCC with respect to the mass of the water-soluble polymer, whereby the NCC hydrogel inhibits bacterial adhesion to the catheter surface to thereby inhibit biofilm formation and inhibit growth of bacteria on the catheter surface.

2. The catheter of claim 1 wherein the catheter surface comprises silica, silicone, polyvinyl chloride, or latex rubber.

3. The catheter of claim 1 wherein the NCC hydrogel further comprises humic acid or a saccharide.

4. The catheter of claim 1 wherein the NCC and water-soluble polymer comprise about 0.1 wt. % to about 10 wt. % of the mass of the NCC hydrogel.

5. The catheter of claim 1 wherein the polymer is a hydroxyalkyl cellulose or a carboxyalkyl cellulose.

6. The catheter of claim 5 wherein the polymer is 2-hydroxyethyl cellulose (HEC) or carboxymethyl cellulose (CMC).

7. The catheter of claim 1 wherein the pH of the NCC hydrogel is about 5.2 to about 7.4.

8. The catheter of claim 1 wherein the ionic strength of the NCC hydrogel is about 5 mM to about 50 mM.

9. A device for preventing catheter associated urinary tract infections on a urinary catheter comprising a catheter coated with a nanocrystalline cellulose (NCC) hydrogel, wherein the NCC hydrogel comprises NCC, a water-soluble polymer, and water; the NCC hydrogel comprises about 1-20 wt. % NCC with respect to the mass of the water-soluble polymer; the pH of the NCC hydrogel is about 6.2 to about 7.3; and the ionic strength of the NCC hydrogel is about 5 mM to about 40 mM.

10. A method of reducing bacterial adhesion to a surface of a medical device comprising contacting bacteria on or in proximity to a surface with nanocrystalline cellulose (NCC), wherein the bacteria are bacteria that produce high amounts of extracellular polymeric substance (EPS), thereby causing flocculation or aggregation, and thereby reducing the adhesion of the bacteria to the surface.

11. The method of claim 10 wherein the bacteria that produce high amounts of extracellular polymeric substance (EPS) comprise *Pseudomonas* fluorescence, *Pseudomonas aeruginosa*, *Salmonella* spp., or *Klebsiella pneumoniae*.

12. The method of claim 10 wherein the bacteria are in a dispersion and form flocs or aggregates in the presence of the nanocrystalline cellulose (NCC).

13. The method of claim 10 wherein the nanocrystalline cellulose (NCC) is present in a coating, film, textile, or reinforcing filler.

14. The method of claim 10 wherein the surface is a silica surface, a silicone surface, a polyvinyl chloride surface, or a latex rubber surface.

15. The method of claim 10 wherein the nanocrystalline cellulose (NCC) is in the form of a hydrogel comprising NCC, a water-soluble polymer, and water, and humic acid or a monosaccharide.

16. The method of claim 15 wherein the hydrogel comprises about 1-20 wt. % NCC with respect to the mass of the water-soluble polymer.

17. A hydrogel composition comprising nanocrystalline cellulose (NCC), a water-soluble polymer, water, and one or both of humic acid and a saccharide, wherein the hydrogel comprises about 1-20 wt. % NCC with respect to the mass of the water-soluble polymer, the NCC and water-soluble polymer comprise about 0.1 wt. % to about 10 wt. % of the mass of the NCC hydrogel, and the humic acid or saccharide is present in a concentration of about 0.1 mg/mL to about 10 mg/mL.

18. The catheter of claim 1 wherein the hydrogel coating comprises nanocrystalline cellulose (NCC), a water-soluble polymer, water, and one or both of humic acid and a saccharide, wherein the hydrogel comprises about 1-20 wt. % NCC with respect to the mass of the water-soluble polymer, the NCC and water-soluble polymer comprise about 0.1 wt. % to about 10 wt. % of the mass of the NCC hydrogel, and the humic acid or saccharide is present in a concentration of about 0.1 mg/mL to about 10 mg/mL.

* * * * *